US005593883A

United States Patent [19]

Cano et al.

[11] Patent Number: 5,593,883
[45] Date of Patent: Jan. 14, 1997

[54] ANCIENT MICROORGANISMS

[75] Inventors: Raul J. Cano, San Luis Obispo, Calif.; Monica K. Borucki, Laporte, Colo.

[73] Assignee: Ambergene Corporation, San Francisco, Calif.

[21] Appl. No.: 330,894

[22] Filed: Oct. 28, 1994

Related U.S. Application Data

[63] Continuation-in-part of Ser. No. 290,319, Aug. 15, 1994, abandoned, which is a continuation of Ser. No. 187,961, Jan. 28, 1994, abandoned.

[51] Int. Cl.$^6$ .................. C12N 1/20; C12N 5/00
[52] U.S. Cl. .......... 435/252.1; 424/93.1; 424/93.4; 424/93.41; 424/93.43; 424/93.46; 424/419; 435/240.1; 435/252.5; 435/252.31; 435/252.34; 435/255.1; 435/255.2; 435/255.21
[58] Field of Search ................... 424/93.1, 93.4, 424/419, 93.41, 93.43, 93.46; 435/240.1, 252.5, 252.1, 252.31, 252.34, 252.35, 252.7, 253.5, 253.6, 254.1, 254.2, 255.1, 255.2, 255.21

[56] References Cited

PUBLICATIONS

Cano et al, "Revival & Id. of Bact. Spores in 25–40 million yr old Dom. Amber", 19 May 1995, V. 268, *Science* 1060–1064.

Garza–Valdes, "Bioplastic Coating on the Shroud of Turin", A Pre. Report Dec. 25, 1993, vol. X pp. 1–46.

Browne, "30 Million–yr Sleep: Germ Declared Alive", New York Times, Cover story vol. CXLIV . . . No. 50,666, May 1995.

Hotz, "Ancient Bacteria in an Amber Tomb Revived", Los Angeles Times, Friday, May 19, 1995.

Hamamoto, T. and Horikoshi, K. "Characterization of a bacterium isolated from amber". *Biodiversity and Conservation* 3:567–572 (1994).

Cano, et al., *Med. Sci. Res.* 20:249–251 (1992).

Goldberg, *Nature* 344:656–658 (1990).

Poinar, G. O., *Life In Amber*, Stanford University Press, Stanford, California (1992).

*Primary Examiner*—David M. Naff
*Assistant Examiner*—Deborah K. Ware
*Attorney, Agent, or Firm*—Albert P. Halluin; S. Leslie Misrock; Pennie & Edmonds

[57] ABSTRACT

The recovery of live ancient bacteria, fungi and other biological material from various sources fossilized in amber or related resins is described. Several ancient bacterial strains have been classified as related to various species of the modern genus Bacillus, for example, based upon their morphological and biochemical characteristics, and enzymatic activity profiles. Although some of the characteristics of the ancient microorganisms correlate well with their modern counterparts, several differences have been observed. In addition, several of the ancient microorganisms described herein exhibit potent antimicrobial activities against modern bacterial and fungal pathogens which attack animals and plants. Various uses for these ancient microorganisms are envisioned, including their use in agriculture, industrial processes, bioremediation, diagnostic and disease treatment.

48 Claims, 1 Drawing Sheet

ANCIENT MICROORGANISMS

REFERENCE TO RELATED APPLICATIONS

This application is a continuation-in-part of application Ser. No. 08/290,319, filed Aug. 15, 1994, now abandoned which is a continuation of application Ser. No. 08/187,961, filed Jan. 28, 1994, now abandoned.

TECHNICAL FIELD OF THE INVENTION

The present invention relates to the recovery of ancient organisms from sources such as amber, and to methods of isolating and culturing such ancient organisms. The invention reveals for the first time that fossilized organisms may be recovered and cultured to present viability. Many uses for the ancient organisms of the invention and their by-products are envisioned, including their use in agriculture, industrial processes, bioremediation, diagnostics and disease treatment.

BACKGROUND OF THE INVENTION

Amber is a natural, amorphous, polymeric glass, fossilized resin from plants having mechanical, dielectric, and thermal features common to other synthetic polymeric glasses, Poinar, G. O., Life in Amber, Stanford University Press, Stanford, Calif. (1992). The plant resins from which amber originates comprise complex mixtures of terpenoid compounds, acids, alcohols, and essential oils. As the resin ages, it becomes harder and forms a semifossilized product known as copal. Recently fossilized tree resins are considered copal (less than about 4 million years old), while older fossilized tree resins are generally considered amber. Amber and copal are better distinguished by studying various physical characteristics, such as melting point, hardness, solubility, and the like.

The oldest amber known was recovered from the Carboniferous Period of the Paleozoic era (360 to 286 million years old). Most of the well studied amber comes from the Cretaceous Period of the Mesozoic Era (65 to 144 million years ago) and the Tertiary Period of the Cenozoic Era (2 to 65 million years ago). For a comprehensive discussion of amber and its characteristics, see, Poinar, supra.

Amber appears to have a remarkable capacity to preserve biological materials, including cell organelles. For example, beginning in this century, scientists have observed the preservation of tissue in amber inclusions, see Poinar, supra at 266∝271. Specifically, well-preserved cells and cell components, including mitochondria and chromatin, have been observed in a 40 million year old fly fossilized in Baltic amber, Poinar and Hess, Science 215:1241–1242 (1982).

More recently, scientists have started to evaluate whether amber is capable of preserving intact ancient genetic material. Beginning in the mid-1980's, for example, scientists attempted to recover viable ancient biological materials, and specifically ancient DNA from a wide range of ancient sources. Early experiments to extract ancient DNA were conducted on museum skins, Higuchi et al., Nature 312:282–284 (1984), Thomas et al., J. Mol. Evol. 31:101–112 (1990), mummified tissues, Paabo, Nature 314:644–645 (1985) and Lawlor et al., Nature 349:785–788, (1991), bones, Hagelberg et al., Nature 342:485 (1989); Hagelberg et al., Phil. Trans. R. Soc. Lond. B. 333:399–407 (1991); Hanni et al., Acad. Sci. Paris Ser. III. 310:365–370 (1990); Hagelberg and Clegg, Proc. R. Soc. Lond. B. 244:45–50 (1991); Horai et al., Phil. Trans. R. Soc. Lond. B. 333:409–417 (1991); Hummel and Herrman, Naturwissenschaften 78:266–267 (1991), plant fossils, Golenberg, Nature 344:656–658 (1990), frozen woolly mammoths, Higuchi and Wilson, Federation Proc. 43:1557 (1984); Cherfas, Science 253:1354–1356 (1991), and ancient seeds, Rogers and Bendich, Plant Mol. Biol. 5:69–76 (1985), Rollo et al., Nature 335:774 (1988). However, these repeated attempts to isolate viable ancient DNA from fossilized materials entombed in amber were met with failure.

The first reported successful isolation of ancient DNA from amber fossils occurred in 1992, when DNA fragments were isolated from extinct bees, Proplebeia dominicana, preserved in 25–40 million year old Dominican amber, Cano et al., Med. Sci. Res. 20:249–251 and 619–622 (1992). Very recently, DNA from a 120–135 million year old weevil preserved in ancient Lebanese amber was PCR amplified and sequenced, Cano et al., Nature 363:536–538 (1993). These reports indicate that amber can, to some extent, preserve ancient genetic information.

Nonetheless, despite the reports of successful recovery of ancient DNA from amber and other ancient materials, considerable skepticism exists within the scientific community as to whether the genetic materials sequenced in these studies is truly ancient or attributable to modern-day contaminants. (See Ancient DNA, Springer-Verlag at 10, 62–64, 158–160, 221–222). Other scientists argue that due to the inherent instability of the DNA molecule, amber, it is impossible for viable DNA to remain intact for millions of years. Lindhal, Nature: 362:709–715 (1993).

Notwithstanding the wealth of work being conducted with respect to the extraction of ancient DNA from various sources, including amber, very little work has been conducted with respect to the recovery of ancient bacteria and other ancient biological materials preserved in amber or similar naturally-occurring resin materials. The meaning of this work further has been hindered by inconclusive results. For example, although bacterial rods and fungal spores (Micrococcus electroni, Bacillus electroni, Longibacillus electroni and Spirillum electroni), as well as pollen, were observed after dissolving amber in turpentine as early as 1929, Blunck, G., Bacterienneischlusse imm Berstein, Centraalblatt fur Mineralogie, Geologie und Palaontoligie (ABt. B, nomII 554–5) (1929), cited in, Poinar, G. O., Life in Amber at 350, Stanford University Press, Stanford, Calif. (1992). These organisms were attributed to modern-day laboratory contaminants. Id.

Similarly, reports of viable bacteria isolated from Paleozoic salts (Dombrosky. H. J., Zentr. Bakteriol. Parasitenk. Abt. I. 178:83–90 (1960); Dombrosky. H. J., Zentr. Bakteriol. Parasitenk. Abt. 1. 183:173–179 (1961)) have been attributed to modern bacterial contaminants, as pools of ancient microorganisms trapped in such soil sediments are likely to have become contaminated with more recent microorganisms via ground water infiltration. In 1983, intact bacterial cells were observed to be preserved in Mexican amber, Poinar, supra. Again, however, neither the age nor authenticity of the cells have been confirmed and contamination by modern bacteria is suspected. The results of each of these attempts to recover viable bacteria from amber thus have been inconclusive.

Intensive commercial development of microbes and microbial by-products for medical, industrial and agricultural applications and bioremediation have occurred during the last 80 years. Harvey, ed., Drugs From Natural Products; Pharmaceuticals and Agrochemicals, Ellis Horwood Ltd., England (1993) which is incorporated herein by reference. For example, the large scale scientific development of antibiotics was triggered in 1928 by work on Penicillin produced by the fungus *Penicillium notatum*. Likewise, intense use of microbial processes for industrial use increased in the 1940's with work on acetone using the anaerobic bacterium Clostridium acetobutylicum, Demain and Solomon, "Industrial microbiology and the advent of genetic engineering," *Scientific American* at pp. 3–11, W. H. Freeman and Co. San Francisco (1981). Relatively few species of microorganisms have presently been exploited for the production of antimicrobial compounds and other microbial by-products for use in medical or industrial processes. For example, only three groups of microorganisms (filamentous fungi, nonfilamentous bacteria and filamentous bacteria, or Actinomyces) are used to produce the bulk of antimicrobial compounds, and industrial microbial by-products.

In addition to producing antimicrobial compounds, microbes produce a wide variety of metabolites that have been used as other pharmaceutical applications including, but not limited to, cardiovascular and anti-inflammatory agents, immunoregulators, anti-tumor compounds, regulators of the central nervous system, and enzyme inhibitors. See e.g., Harwood, C. R., Biotechnology Handbooks: *Bacillus* at 294 et seq., Plenum Press, New York (1989). Microbial metabolites also serve as platform molecules for synthetic chemistry and rational drug design and are widely used as the basis of vaccine production. See, Harvey, ed., *Drugs From Natural Products; Pharmaceuticals and Agrochemicals*, Ellis Horwood Ltd., England (1993).

Microbes and microbial by-products have also been used in a variety of industrial processes, such as enzyme and vitamin production and fermentation. For example, *B. subtilis* produces a variety of thermostable serine protease enzymes that are widely used in laundry detergents. Id. Various species of fungi, including Saccharomyces, Aspergillus and Candida are used in the production of beer, wine, sake and other food products, as well as a variety of vitamins. Microbial by-products are also used in the production of cosmetics, biopolymers, surfactants, purine nucleosides, and phenolic germicides. Id.

More recently, due to increasing concern over environmental pollution, microbes and microbial by-products are being used for biopesticides and bioremediation. For example, *B. sphaericus* and *B. thuringiensis* are used commercially as biopesticides to combat a variety of plant and insect pests. See, Harwood at 309, supra. Similarly, species of bacillus, are routinely used in environmental clean-up of toxic pollutants. Id. at 313; Debabov, "The Industrial Use Of Bacilli" in *The Molecular Biology Of The Bacilli*, Vol. 1 (D.A. Dubnau, ed.), Academic Press, New York (1982) at 331–370, which is incorporated herein by reference.

Additionally, microbes and microbial by-products have been increasingly used in diagnostic assays. For example, B. subtilis is used in assays to detect streptomycin, penicillin and cathomycin. See, ATCC Catalog at 34 (1994) citing *J. Bact.* 45:408–409 (1943), *J. Bact.* 49:411 (1945), *Appl. Microbiol.* 4:307–310 (1956).

Changing patterns in animal and human health, agricultural, industrial and environmental processes demand a search for new sources of microbial by-products for medical, diagnostic and industrial applications. For example, numerous pathogenic microorganisms have become resistant to antibiotics currently derived from modern microorganisms, Cooksey, R. C., "Mechanisms of resistance to antimicrobial agents," Manual of Clinical Microbiology at 1099, 5th. Ed., Am . Soc. for Microbiology (1991). Similarly, many widely used agrochemicals have been shown to be toxic to flora and fauna and to cause contamination to water resources. Growing resistance to traditional antimicrobial compounds, new demands created by modern industrial processes, the need to develop alternatives to chemical pesticides and herbicides, and the need to eliminate environmental contaminants create opportunities for using novel microbes and their by-products. A comprehensive summary of the identity and existing uses of the microbial by-products known to date is set forth in *Biotechnology*, volumes 1–8, H. J. Rehm and G. Reed, editors, Verlag Chemie (1986), which is incorporated herein by reference.

SUMMARY OF THE INVENTION

The present invention relates to the recovery of ancient organisms and biological materials from sources capable of preserving such biological materials and organisms for many millions of years. More specifically, the invention relates to ancient microorganisms isolated from amber and similar naturally-occurring resins. Such microorganisms include but are not limited to bacteria, fungi, protozoa, viruses and microalgae. Additionally, the present invention is directed to the recovery of ancient organisms and biological matter from amber and similar naturally occurring resins, including pollen, plants, arthropods of different groups and nematodes.

The invention is based upon the extremely surprising discovery that ancient microorganism strains can be recovered and revived to a viable state after being fossilized in amber for over 25,000,000 years. In a particular embodiment of the invention, described more fully below, more than a dozen viable strains of ancient Bacillus bacteria were isolated from the preserved abdominal cavity tissues of four ancient stingless bees, *Proplebeia dominicana*, fossilized in Dominican amber some 25 to 40 million years ago. Amber samples used to recover the ancient Bacilli of the invention were rigorously authenticated, extractions and sterile culturing conditions were designed to eliminate the possibility of contamination with modern microorganisms, and various controls and mock extractions were conducted to verify the ancient status of any viable microorganism resulting from the extractions.

In order to prove the antiquity of the amber-derived organisms, modern Bacillus sp. were isolated from the abdominal cavity of the modern descendant of the amber-entombed bee and compared with the ancient Bacillus isolates via taxonomic, biochemical and genetic analysis. Portions of the 16 S rDNA of both the ancient and modern day bacterial isolates were amplified using PCR and sequenced. The sequences of the modern and ancient Bacillus were compared and found to have approximately 93–95% homology. Using the "molecular clock" analysis described more fully below, the nucleotide substitution rates of several of the ancient isolates were calculated. On the basis of these calculations, the ancient organisms were determined to be approximately 50 million years-old, which is consistent with the approximate age of the Dominican amber (25–40 million years old) from which they were isolated.

As a result, there is no doubt that the Bacilli isolated by applicants and described herein are indeed recovered ancient organisms which have remained dormant for between 25 and 40 million years.

In another particular embodiment of the invention, more than 10 diverse non-Bacillus ancient microorganisms were isolated from many types of biological inclusions within a variety of copals and ambers ranging in age from 250 years to 120 million years. These organisms include, but are not limited to, species of Actinomyces, Streptomyces, Penicillium, yeasts, and Pseudomonas.

These ancient microorganisms are described in terms of their morphological, biochemical, and enzymatic profiles, and are expected to have a number of agricultural, industrial, environmental and medical uses, including but not limited to the production of various commercially useful pharmaceutical products, enzymes (e.g., proteases, amylases, etc.) and preservatives, as biological insecticides, and in a variety of industrial processes. In addition, certain of these ancient microorganisms secrete antimicrobial substances that exhibit the ability to inhibit the growth of certain modern animal pathogens such as streptococcus and staphylococcus, as well as certain agricultural pathogens such as *Erwina carotovora* and may therefore be used for the production of antibiotics. Ancient microorganisms and particularly ancient bacilli may also be used as hosts for recombinant DNA vectors. The ancient microorganisms and the substances they secrete may also have application in the fields of environmental clean-up, mining, diagnostics and food production.

Similarly, ancient microorganisms and their by-products may have useful industrial applications. For example, modern microorganisms presently are important producers of industrial enzymes: strains of yeast such as Saccharomyces sp. are used in the brewing of alcoholic beverages. Such yeast can also be found in soil and sediment samples. See generally, Demain and Solomon, *Biology of Industrial Microorganisms,* Benjamin/Cummings Publishing Company, (1985). Microorganisms are also currently used as biopesticides such as *Bacillus sphaericus* and *Bacillus thuringiensis* are often found associated with insects. Mitscherlich and Martin, *Microbial Survival in the Environment,* Springer-Verlag (1984). This information is useful in identifying sources of biological material within the amber or resin from which ancient microorganisms with potential commercial applications might be derived. However, because these ancient microorganisms differ genetically from their modern day counterparts, one might expect that the ancient microbes are capable of producing different by-products with potentially novel chemical structures.

DETAILED DESCRIPTION OF THE INVENTION

Ancient Microorganism Deposit Diversity

Figure 1:
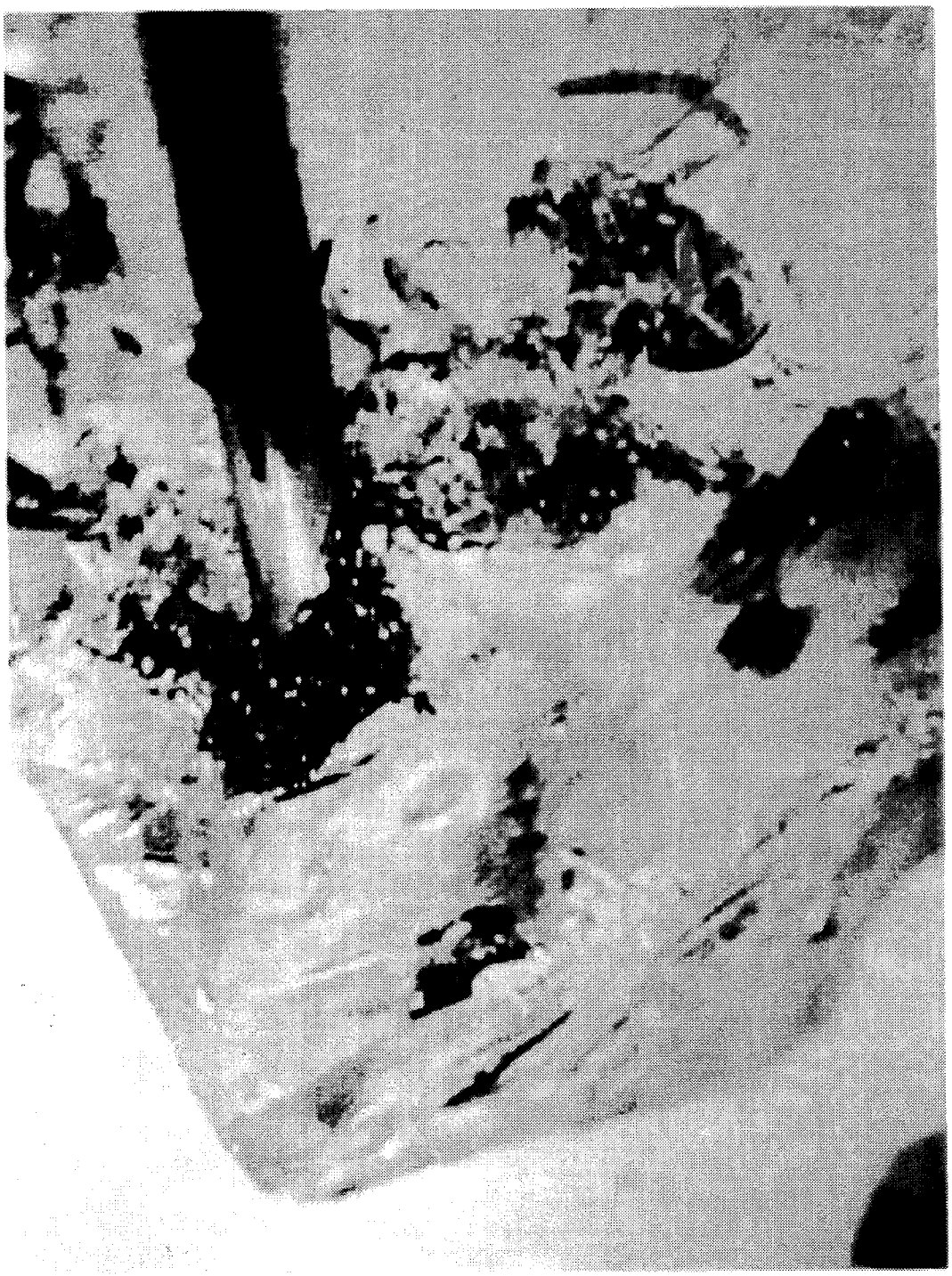
FIG. 1. Photograph of sample being extracted from abdominal tissue of an ancient stingless bee fossilized in amber dating 25–40 million years old.

Organisms which may be recovered from amber and related naturally-occurring resins include but are not limited to bacteria, fungi, protozoa, viruses, microalgae, pollen, plants (mosses and lichens, ferns, and higher plants), arthropods of different groups, and nematodes. One aspect of the invention relates to isolating ancient microorganisms, such as bacteria, and particularly endospore forming bacteria including but not limited to members of the Bacillus genus.

Other aspects of the invention relate to isolating ancient microorganisms, such as bacteria and fungi, including but not limited to, members of the genus Actinomyces, Streptomyces, Saccharomyces, Aspergillus, Penicillium, Micrococcus, Arthrobacter, Coryneform and Pseudomonas. Additional aspects of the invention relate to isolating ancient microorganisms, including but not limited to organisms such as bacteria and fungi, that are capable of growing under extreme conditions, including but not limited to, extreme ranges of both pH and temperature.

Ancient Microorganism Sources

Ancient organisms and biological materials may be recovered from amber and related naturally-occurring resins from diverse geographical locations and ranging in age from approximately 50 years old to over 120 million years old. Organisms may be recovered not only from the resin matrix itself, but also from a broad variety of inclusions found entombed within the resin, including plant spores, microbial spores, soil samples, water and gas bubbles, microbes, fungi, protozoa, insect nests, insect feces, insects, plant materials such as leaves, sticks, bark, roots, flowers, grasses, ferns, legumes, and seed pods, pollen, nematodes, arthropods and shells.

Authentic amber or similar naturally-occurring resins may be found in several regions of the world, including Burma, the Dominican Republic, the Baltic Sea region, Canada, China, Colombia, Sumatra, Chiapas, Luzon, Romania, Sicily, the Arctic coast of Alaska, Northeastern U.S.A., the Cedar Lake region of Manitoba, Northern France, Lebanon, Israel, Jordan, and Eastern Taimyr (Soviet Arctic). It is important to verify that the source from which ancient organisms or biological materials are recovered is indeed authentic. In addition to carefully tracking and verifying the source of a resin sample, a sample's age may be determined indirectly by examining the fossils found in the strata from which the sample was taken, if possible. The age of fossils surrounding the fossilized resin deposit provides an idea of the age of the fossilized resin. For example, some shell-forming protozoa were abundant at a particular geological time, and if fossils of such protozoa are found along with amber it can be assumed that the amber was formed during that geological period. Other methods for authenticating, characterizing, and directly dating a sample include x-ray diffraction, nuclear magnetic resonance spectroscopy, pyrolysis gas chromatography and infrared spectroscopy (see generally, Poinar, supra).

Information relating to known habitats of modern day organisms can be used to identify potential sources of the ancient organisms of the instant application.

For example, knowledge of present day relationships between various microorganisms and insects may provide guidance for identifying sources from which ancient microorganisms may be recovered. For example, bees and various organisms appear to utilize symbiont microorganisms to protect themselves from pathogens as well as to process and preserve their food. Thus, based on current knowledge of such microbial symbionts of bees, one can infer that bee ancestors also used microbial symbionts to fight ancient bee pathogens as well as to process and preserve their food. More specifically, the tropical stingless bee Melipona fasciata appears to use spore-forming bacteria to preserve food in their nests. Various Bacillus organisms have been isolated from food stored in *M. fasciata* nests, including *B. megaterium, B. circulans* and *B. alvei*, Gilliam et al., *Apidologie* 21:89–97 (1990). Based on the biochemical properties of these bacteria, the authors suggested that those bacteria were used by the bees to preserve and process their food. Other cases of associations between bacteria and bees have been reported. For example, *B. brevis, B. megaterium, B. coagulans, B. cereus,* and *B. subtilis* have been isolated from various organs of the honey bee, *Apis mellifera,* Gilliam et al., *J. Invert. Pathol.* 31:389–391 (1978). *B. subtilis* and *B. cereus* have also been isolated from the solitary bee Craw-

*fordapsis luctuosa,* Gilliam et al., *Apideologie* 21:99–105 (1990).

In addition to bacteria, yeast appear to play a role in processing pollen collected by the bees, Gilliam et al., *Apidiologie* 10:53–53 (1979). Some bacteria isolated from bees or bee's nests (e.g., *B. subtilis*) produce antibiotics such as mycosubtilin, Besson et al., *J. Antibiotics* 29:1043–1049 (1976). Accordingly, it has been suggested that such symbiont bacteria assist the bees in protecting themselves from pathogens, Gilliam et al., *Apidiologie* 21:99–105 (1990). While similar roles may have been played by ancient microbial symbionts in ancient bees, it is likely that such microbial ancestors produced some substances for which no exact modern equivalents exist given the very different environmental conditions such as temperature, gas concentrations, and communities of pathogens that existed during ancient times.

Similarly, antibiotic producing microorganisms such as Actinomyces, Streptomyces, Penicillium and Cephalosporium are commonly found in soil habitats or are associated with plant materials. Likewise, microorganisms that are known producers of industrial enzymes, such as *Bacillus subtilis,* are also found in soil habitats. Strains of yeast such as Saccharomyces sp. used in the brewing of alcoholic beverages can also be found in soil and sediment samples. See generally, Demain and Solomon, *Biology of Industrial Microorganisms,* Benjamin/Cummings Publishing Company, 1985). Microorganisms that are currently used as biopesticides such as *Bacillus sphaericus* and *Bacillus thuringiensis* are often found associated with insects. Mitscherlich and Martin, Microbial Survival in the Environment, Springer-Verlag (1984). Again, because the ancient microorganisms differ genetically from their modern day counterparts, one might expect that the ancient microbes are capable of producing different by-products with potentially novel chemical structures.

Methods For Isolating And Culturing Ancient Microorganisms

Various methods for isolating microorganisms, organisms and other biological material directly from amber or a similar naturally-occurring resin or from organisms fossilized in such amber or resin may be used in practicing one aspect of the invention, provided that adequate containment and contamination safeguards are employed. One such safeguard involves sterilization of the outer surface of a resin sample containing fossilized biological material or organisms.

In a preferred embodiment of this invention, the outer surface of an amber sample is sterilized as follows: the amber sample is: (1) weighed in a tared weighing boat; (2) immersed in 2% buffered glutaraldehyde at 35° C. for 12 hours in vacuo; (3) rinsed three times in sterile, double distilled water (SDDW) and then culturing the rinse water on Trypticase Soy agar (TSA) (BBL, Cockeysville, Md.) to evaluate the effectiveness of the sterilization procedure; (4) immersed in 10% bleach for an additional 6 hours at 37° C.; (5) rinsed three times in SDDW and then culturing the rinse water on TSA to evaluate the effectiveness of the sterilization procedure; (6) immersed in 70% ethanol for 2 hours at 35° C.; and (7) exposed to flames to evaporate the alcohol. A sample of this surface-sterilized amber is cultured onto Triptycase Soy Broth (TSB) to evaluate the sterilization process.

Other methods of sterilizing and/or decontaminating amber and/or other naturally-occurring resin samples include plasma etching, sonication, fixatures, solvents, gas fumigation, application of a sporicidal agent and removing the outer layer of the resin from the sample.

Samples of the fossilized material are then extracted using sterile instruments, sterile techniques, and under sterile conditions. For example, amber may be cracked after freezing in liquid nitrogen in order to expose the specific tissue of the entombed fossil. Additionally, samples with or without visible biological materials, minerals, or organism fossils, may be ground and/or pulverized into powder or semi-powder material under sterile conditions following decontamination of the sample's surface. The samples may be ground into a powder or semi-powder by any number of methods, including use of sterile sand or a mortar and pestle. Less destructive and more targeted methods of isolation may provide the dual advantages of sample preservation and control over which part of a fossil or other inclusion is removed for recovering the ancient microorganisms. Such methods may include, for example, the use of hollow-bore micro-drills capable of extracting very small samples of a fossil or other inclusion without destroying the entire sample. Such methods may further include use of techniques for freezing the resin sample, directed laser(s), use of sterile sand to grind the sample into powder, heat, use of a sterile pulverizing press and chemical treatment. Hydration of the desiccated fossil may facilitate sample extraction.

Extracted samples may then be placed into various types of growth media presently used for propagating microorganisms and under various conditions in order to recover viable ancient microorganism cultures within the contained and decontaminated environment.

Varying the conditions under which the ancient microorganisms are allowed to generate viable cultures may be used to target the isolation to a particular type of microbe. For example, by adjusting the growth temperature to extremes, one can culture microorganisms which are capable of growing under unusual conditions, while selecting-out other microorganisms not capable of surviving such conditions. Growth media components may also be adjusted for selection purposes. In addition to the methods described herein, other sterilization methods and growth conditions not explicitly described herein will be readily apparent to those skilled in the art and may also be used to maintain proper contamination safeguards, as well as to isolate and propagate ancient microorganisms.

In one embodiment of the present invention, ancient microorganisms are extracted from sterilized amber or similar naturally-occurring resin sample by pulverizing such resin sample ("pulverizing extraction method") and then culturing the extracted microorganism. Specifically, the following protocol may be followed:

1. Sterilize the resin sample as described above.

2. In safety cabinet, place surface-sterilized sample in sterile mortar within a safety cabinet and flood with liquid nitrogen.

3. Crush and pulverize super-cooled amber with sterile pestle or by placing super cooled amber through sterile pulverizing press.

4. Distribute amber powder equally into each of four 250-ml erlenmeyer flasks with 25 ml of the following sterile broths: (a) Actinomycete broth (Difco); (b) 1% peptone (2 flasks); and (c) tomato juice agar (Difco).

5. Incubate one of the flasks containing 1% peptone at 55° C. and the remaining three flasks at 30° C. in an orbital shaker at 200 RPM.

6. Sample 500 µl and spread daily for the first week from each of the flasks then weekly for four weeks onto the following media: (a) TSA; (b) potato dextrose agar (PDA), (c) Czapek agar (Difco) with 0.4% yeast extract; (d) plate count agar (Difco) with 2% sterile skim milk (SMA); (e) SMA pH 8.1; and (f) starch agar (Difco). Incubate each plate at the appropriate temperature (plates to be incubated at 55° C. are to be placed inside a sterile sealable bag with moistened sterile paper towels or sponge).

7. Examine plates daily for the presence of colonies.

8. Pick isolated colonies and subculture each microbial isolate onto appropriate culture media. Freeze (at −80° C.) each colony on the plate. Perform Gram stain to evaluated morphology and gram-staining characteristics of each isolate. Fungi and yeasts are to be examined in wet mounts of lactophenol cotton blue mounting medium.

9. Freeze and lyophilize at least 10 isolates from each plate. At this point, FAME (fatty acid methyl ester) analysis should be performed on each isolate to establish the degree of genetic diversity within each population.

In this method, the sample may be pulverized without use of liquid nitrogen.

In a second method, the amber or similar naturally-occurring resin is "cracked" after sterilization to extract ancient microorganisms ("cracking extraction method") and then such microorganisms are cultured. Specifically, the following protocol may be used:

1. Sterilize the amber or similar naturally-occurring resin as described above.

2. In safety cabinet, place the sterilized sample with desired inclusion on sterile Petri dish bottom and flood with liquid nitrogen. Allow liquid nitrogen to evaporate completely. Apply several drops of hot sterile saline to the outside of the supercooled sample.

3. With sterile 27-gauge needles, crack sample piece to expose desired tissue.

4. Harvest tissue with sterile needles and transfer into each of two 1.5-ml sterile microcentrifuge tubes containing sterile 1% tryptone broth.

5. Heat-shock one of the tubes in a water bath set at 80° C. for 15 minutes then incubate both tubes at 30° C. in a suitable incubator or dry bath.

6. Streak a loopful daily for the first week from each of the tubes then weekly for four weeks onto the following media: (a) TSA; (b) PDA, (c) Czapek agar (Difco) with 0.4% yeast extract; (d) SMA; (e) SMA pH 8.1; and (f) starch agar (Difco). Incubate each plate at 30° C. and examine plates daily for the presence of colonies.

7. Pick isolated colonies and subculture each microbial isolate onto appropriate culture media. Freeze (at −80° C.) each colony on the plate. Perform Gram stain to evaluated morphology and gram-staining characteristics of each isolate. Fungi and yeasts are to be examined in wet mounts of lactophenol cotton blue mounting medium.

8. Freeze and lyophilize at least 10 isolates from each plate. At this point, FAME (fatty acid methyl ester) analysis should be performed on each isolate to establish the degree of genetic diversity within each population.

In a third embodiment, the ancient microorganism or biological material is extracted from a sterilized amber or other naturally-occurring resin sample by drilling ("drilling extraction method") and then cultured according to the following protocol:

1. Sterilize the amber as described above.

2. In safety cabinet, place amber piece with desired gas, water or liquid inclusion on sterile Petri dish on a drop of fast-setting glue. Wait until the glue hardens to proceed (about 5 minutes).

3. With sterile 0.5 mm to 1.0 mm titanium drill bit attached to a sterile drill press, drill a hole in the amber being careful to pierce the gas, water or liquid bubble.

4. Collect the gas, water or fluid from within the amber inclusion with a sterile, micropipet tip attached to a Drummond micropipet. Transfer the gas, water or fluid into a 1.5-ml sterile microcentrifuge tubes containing sterile 1% tryptone broth.

5. Incubate the tube at 25°–30° C. in a suitable incubator or dry bath.

6. Streak a loopful daily for the first week from the tube then weekly for four weeks onto the following media: (a) TSA; (b) PDA, (c) Czapek agar (Difco) with 0.4% yeast extract; (d) SMA; (e) SMA pH 8.1; and (f) starch agar (Difco). Incubate each plate at 25°–30° C. and examiner the plates daily for the presence of colonies.

7. Pick isolated colonies and subculture each microbial isolate onto appropriate culture media. Freeze (at −80° C.) each colony on the plate. Perform Gram stain to evaluated morphology and gram-staining characteristics of each isolate. Fungi and yeasts are to be examined in wet mounts of lactophenol cotton blue mounting medium.

8. Freeze and lyophilize at least 10 isolates from each plate. At this point, FAME (fatty acid methyl ester) analysis should be performed on each isolate to establish the degree of genetic diversity within each population.

In a fourth embodiment, the ancient microorganism or biological material is extracted from the sterilized fossilized resin by drilling (to the tissue of organism or insect fossil and hydrating the desiccated tissue in peptone broth)("drilling extraction method") and then cultured according to the following protocol:

1. Sterilize the amber as described above.

2. In safety cabinet, place amber piece with desired inclusion on sterile Petri dish on a drop of fast-setting glue. Wait until the glue hardens to proceed (about 5 minutes).

3. With sterile 0.5 mm to 1.0 mm titanium drill bit attached to a sterile drill press, drill a hole in the amber being careful to pierce through the inclusion.

4. Flush the tissue within the inclusion with 50 µl of sterile 1% peptone broth with a sterile micropipet tip attached to a Drummond micropipet. Transfer the fluid into a 1.5-ml sterile microcentrifuge tubes containing sterile 1% tryptone broth.

5. Incubate the tube at 25°–30° C. in a suitable incubator or dry bath.

6. Streak a loopful daily for the first week from the tube then weekly for four weeks onto the following media: (a) TSA; (b) PDA, (c) Czapek agar (Difco) with 0.4% yeast extract; (d) SMA; (e) SMA pH 8.1; and (f) starch agar (Difco). Incubate each plate at 25°–30° C.

7. Pick isolated colonies and subculture each microbial isolate onto appropriate culture media. Freeze (at −80° C.) each colony on the plate. Perform Gram stain to evaluated morphology and gram-staining characteristics of each isolate. Fungi and yeasts are to be examined in wet mounts of lactophenol cotton blue mounting medium.

8. Freeze and lyophilize at least 10 isolates from each plate. At this point, FAME (fatty acid methyl ester) analysis should be performed on each isolate to establish the degree of genetic diversity within each population.

For each of these protocols, three plates of TSA may be placed in the hood to test for environmental contaminants. The plates are left open throughout the entire extraction procedure. At the end of the procedure, the Petri plate lids are replaced and the plates incubated at 35° C. for two weeks.

Identifying And Characterizing Ancient Microorganisms

Various general and specific methods of identifying and characterizing modern-day microorganisms may be used to identify and characterize ancient microorganisms of the invention. In this regard, ancient microorganisms may be evaluated morphologically, biochemically, genetically, and biologically. For example, an ancient bacterium may be examined visually with and without magnification to assess various morphological characteristics. Stain affinities, endospore characteristics, and growth conditions are also generally assessed. Biochemical characteristics such as those typically used to classify modern-day microorganisms may also be used to characterize the ancient bacteria. Additionally, ancient microorganisms may be tested for the production of a wide range of enzymes characteristic of various modern-day organisms as a means for drawing relations or distinctions between modern and ancient organisms. Moreover, ancient organisms may be tested for the production of antibiotics and/or other biologically active substances using techniques well known to those in the art, not only as a means for identifying and characterizing the organisms, but also for identifying useful biologically active molecules produced by the organisms.

Ancient organisms may be further characterized by evaluating their genetic information. One approach to genetic analysis involves amplifying ancient nucleic acids using any suitable DNA or RNA amplifying technology, such as the polymerase chain reaction or the ligase chain reaction methodologies, using primers designed from gene sequences of modern-day organisms. Genes of the ancient organism which may be related to genes of modern-day organisms is to be cloned and sequenced to evaluate genetic relatedness and evolutionary divergence, and to determine the structure of the proteins encoded therein. Alternatively, genetic information of ancient microorganisms may be isolated using random primer amplification or sequence independent primer amplification techniques known in the art. In addition, cultures of ancient microorganisms may be used to isolate large quantities of genomic DNA from sequence analysis.

In one embodiment of the present invention, DNA is extracted from putative ancient microbial isolates and a segment of the 16 S rRNA gene is amplified using appropriate primers. PCR amplifications are performed using 1 unit of low-DNA Taq polymerase (AmpliTaq-LD DNA polymerase, Perkin Elmer, Norwalk, Conn.), 2 µg/ml bovine serum albumin fraction V (Sigma, St. Louis, Mo.), 0.5 µM each of the primers, 2.0 mM $MgCl_2$, and 0.2 mM deoxynucleotide triphosphates (dNTPs) in a total volume of 50 µl. All reagent mixtures and sample dilutions are performed in an ice water bath and the tubes placed in the thermal cycler after the heat block reached 80° C. Polymerase chain reactions are performed using a thermal cycler dry bath with the appropriate protocol (optimized using the appropriate template DNA and primers). PCR products are cloned into suitable cloning vectors and then sequenced using standard protocols.

Dating The Ancient Microorganisms

Using the PCR amplification technique described above, the age of an ancient microorganism may be determined. Following sequencing, the sequences may be aligned either manually or with the aid of an alignment software package and the sequences evaluated. The rate of nucleotide substitution for 16 S rRNA genes, r, is assumed to be $0.3-0.4 \times 10^{-9}$ substitutions per position per year based on previous reports, Ochman, H. & Wilson, A. C. *J. Mol. Evol.* 26:74–86 (1987); Moran, N. A., Munson, M. A., Baumann, P., & Ishikawa, H. *Proc. R. Soc. Lond. B.* 253:167–171 (1993). The time of divergence between the two taxa (the age of the amber from which the putative ancient microorganisms was isolated) is determined by dividing the number of substitutions between the putative ancient organism and its closest extant relative by 2 r times the number of nucleotides analyzed. The time of divergence between the two taxa should be roughly the same as the age of the amber from which the isolate was obtained.

Producing Useful Proteins With Ancient Microorganisms

Ancient microorganisms may produce enzymes and other proteins which, although related to proteins produced by modern microbes, are biologically active at higher temperatures, at different atmospheric conditions, and/or against different substrates, etc. As an example, ancient bacteria used by ancient bees to process and preserve their food thrived under different environmental conditions, and may have exhibited biochemical pathways that led to the production of novel metabolites that may have industrial uses. Thus, ancestral enzymes produced by ancient microorganisms are expected to have unique and industrially useful biochemical characteristics such as, for example, optimal performance at higher temperatures or at extreme pH conditions.

Thus, one embodiment of the invention relates to culturing ancient microorganisms for the production of various substances, including but not limited to proteins and enzymes having industrial, agricultural, medical and diagnostic uses. Such substances may be isolated from the cultures directly, and preferably purified, using various techniques currently used for the isolation and purification of similar substances from modern-day microorganisms. Alternatively, such proteins and enzymes may be chemically synthesized or may be produced using recombinant DNA technology.

In a particular embodiment of the invention, ancient Bacillus bacteria isolated from 25 to 40 million year old insect fossils in amber may be used for the production of various useful proteins and enzymes, including but not limited to amylases, lipases, phosphatases and proteases. In addition, certain of ancient Bacilli of the invention may be used to produce antibiotics with variable, enhanced or markedly broader host-range characteristics in relation to their modern descendants. The capacity of an ancient bacilli or other microorganism to produce such proteins may be gauged using the biochemical and enzymatic assays as described below or other well known and widely used assays, e.g., Gordon et al., The genus Bacillus USDA Handbook 427 (1973); API ZYM enzymatic profile tests, described below. For a complete discussion of the various enzymes and other products produced by bacteria of the Bacillus genus, assays for their identification, production methods, and various industrial and other uses, see, Harwood, C. R., Biotechnology Handbooks: *Bacillus,* Plenum Press, New York (1989), the entirety of which is hereby incorporated by reference herein.

In one embodiment of the present invention, one of the ancient Bacilli, designated "BCA 5" produced, among other compounds, acid phosphotase. See, Table III. In separate embodiments of the invention, ancient *Bacillus subtilis*-like organisms produced alkaline phosphatase, butyrate esterase, caprylate esterase and/or β-galactosidase, (see, Example 3), an ancient *Bacillus sphaericus*-like organism produced caprylate esterase and chymotrypsin (see, Example 3), ancient *Bacillus cereus*-like organisms produced alkaline phosphatase, butyrate esterase, caprylate esterase, leucine aminopeptidase, chymotrypsin, acid phophotase and β-glucoronidase and ancient *Bacillus pumilus*-like organisms produced caprylate esterase.

The present-day counterparts to these ancient enzymes have been broad commercial applications, including use in assays for determining protease and amylase activity, leather bating, preventing protein hazes forming in beer, reducing the gluten content of flours, and as an inclusion in household washing detergents. See e.g, Harwood, C. R., Biotechnology Handbooks: *Bacillus* at 294 et seq., Plenum Press, New York (1989) which is incorporated herein by reference. See also, above discussion. Although the ancient microbes producing the enzymes are not identical to their present-day counterparts, the commercial application of the modern microbe produced enzymes suggests the application of the enzymes produced by ancient microbes over a vast array of uses in commercial settings. For example, one form of *Bacillus subtillis*-like microbe, discussed below, was shown to produce an active and stable alkaline protease. See, Example 3.

Antibiotics And Antimicrobial From Ancient Microorganisms

Ancient microorganisms may have produced antibiotics effective against various ancient organisms that either no longer exist or are less prevalent or effective in today's microbial world. The evolution of modern microorganisms is likely to have been accompanied by the loss of certain characteristics which enabled their ancestors to resist the antimicrobial action of their ancient microbial neighbors. Ultimately, some microorganisms may have evolved to the point of being incapable of defending themselves against the same pathogens their ancestors were readily able to resist, perhaps simply because of a dwindling prevalence of such ancient pathogens over great periods of time. In this connection, antimicrobial substances once vital for survival in ancient times may have eventually become completely unnecessary or redundant, and accordingly, time and evolution may have led to modern microorganisms which no longer produce these active substances. Thus, antibiotics from ancient microorganisms may be extremely effective for the treatment of modern microbial infections, particularly those caused by new and rapidly evolving antibiotic-resistant pathogenic strains. The invention therefore provides medical science with an opportunity to go back in time and examine the antimicrobial properties of microorganisms that lived millions and millions of years ago in the midst of various life forms that have long been extinct, and within an environment that was radically and fundamentally different from what it is today.

Thus, another embodiment of the invention relates to the production of antibiotics using ancient microorganisms. More particularly, certain ancient Bacillus and Actinomycete strains isolated by applicants and described more fully below, demonstrate powerful antimicrobial activity against human microbial pathogens. Although many of the ancient Bacilli and Actinomycete demonstrate antimicrobial activities against various strains, in general the ancient bacilli identified as *B. subtilis*-like and *B. lichenformis*-like appeared to produce the strongest antimicrobial activities. One of the ancient Bacilli, designated "BCA 1" and identified as a *B. subtilis*-like bacteria, is capable of totally inhibiting the growth of *Staphylococcus aureus* and *Streptococcus pyogenes*. Additionally, BCA 1 is also capable of inhibiting the growth of *Salmonella pullorum*, *E. coli*, *Agrobacter tumefaciens*, *Acinetobacter calcoaceticus*, *Erwinia caratovora*, *Verticillium dahliae*, and *Penicillium notatum*. Thus, BCA 1 produces a very powerful antibiotic which is expected to be useful in treating infections caused by various pathogenic microbes. Ancient Bacilli BCA 12, BCA 13, and BCA 15, all identified as *B. lichenformis*-like strains, may be useful for the production of a molecular ancestor of modern-day bacitracin derived from *B. lichenformis*.

Methods for testing the antimicrobial activity of microorganisms have long been known in the art and may be employed equally well with the ancient microorganisms of the invention. Such methods include, for example, the routinely used cross-streak method, Colome et al., Laboratory Exercises In Microbiology, West Educational Publ., St. Paul, Minn. (1986), as well as those described by Chatterjee et al. in *J. Antibiotics* 45(6):832–838. Both the Colome et al. and Chatterjee et al. references are incorporated herein by reference.

Other useful agents, including antimicrobial, anti-cancer, anti-inflammatory, CNS, cardiovascular and chemotherapeutic agents may also be produced by the ancient microorganisms. Harvey, ed., *Drugs From Natural Products; Pharmaceuticals and Agrochemicals*, Ellis Horwood Ltd., England (1993)

Other Uses For Ancient Microorganisms

In yet another embodiment of the invention, ancient microorganisms may be used in the biological control of insects. For example, certain species of Bacillus are currently used to control insect populations, such as *Bacillus thuringiensis* and *Bacillus popillae*, which are among the most successful of all microbial control agents in use today. Additionally, some strains of *Bacillus sphaericus* appear to be pathogenic for mosquito larvae, and recent field trials suggest that *B. sphaericus* could be a valuable alternative to chemical insecticides. Two of the ancient Bacillus organisms isolated by applicants and described herein, designated "BCA Ex 2" and "BCA 16" have been identified as *Bacillus sphaericus*-like strains on the basis of various morphological and biochemical characteristics. These ancient strains may be pathogenic to modern-day insects and may therefore be useful as biological insecticides.

Ancient microorganisms, and particularly ancient Bacillus bacteria, may also be used as cloning and expression hosts in the production of various proteins. For example, *Bacillus subtilis* is now widely used in recombinant DNA technology and has the advantage of being able to readily secrete high levels of recombinant products. Similarly, ancient microorganisms, and particularly ancient Bacillus bacteria, may also be used as a reagent in diagnostic assays. For example, *Bacillus subtilis* is widely used in diagnostic assays for the detection of streptomycin.

The ancient microorganisms of the present invention also have industrial applications. For example, a Saccharomyces sp. isolated from Dominican amber ferments glucose, sucrose, lactose, and galactose with the production of $CO_2$ (gas) and ethanol (alcohol) and may be used in any number of fermentation processes. Demain and Solomon, *Biology of Industrial Microorganisms*, Benjamin/Cummings Publishing Company, 1985). The ancient microorganisms may also be used as biopesticides. *Bacillus sphaericus* and *Bacillus thuringiensis* are currently being used as a biopesticide, indicating that their ancient counterparts could possess similar utility. Mitscherlich and Martin, *Microbial Survival in the Environment*, Springer-Verlag (1984).

Modern day microbial metabolites are also used as antifungal compounds. For example, griseofulvin, used in the treatment of a variety of fungal diseases, is produced by Penicillium sp. Pyrrolnitrin, a topical antifungal agent is produced by different Pseudomonas sp. and also shows some anti-protozoal activity. Variotin, also a topical antifungal treatment, is a product of the fungi Paecilomyces variottii. Siccanin, used in the treatment of fungal diseases of the skin is derived from *Helminthosporium siccans*, a parasitic mold of rye grass. See Biotechnology supra, Vol 4, 248–486.

Likewise, modern antimicrobial compounds produced by microorganisms are also used as additives to animal feed, and to treat certain animal diseases, to protect cultured plants against bacterial, fungal and viral infections, parasitic insect diseases and competitive herbs, to treat certain metabolic disorders such as diabetes, uterine atonia, migraine headaches, orthostatic circulatory disturbances, senility, hypertension, hyperprolactimenia, acromegaly and Parkinson's disease, cancer, cardiovascular diseases, hypercholesterolemia, arteriosclerosis and coronary disease. See *Biotechnology*, volume 4 at 510–620, supra. Microorganisms are also known to produce a variety of vitamins and coenzymes (see, *Biotechnology*, volume 4 at 115–159, supra), and have the ability to accumulate heavy metals and radionuclides from their external environment (see, *Biotechnology*, volume 6b at 402–403, supra). Similarly, the ability of microorganisms to leach metals is used in the mining and metallurgical industries. These known uses of the by-products of modern day organisms provides evidence that the by-products of their corresponding ancient progenitors may be similarly used.

The invention, having been described, the following examples are offered to illustrate the subject invention by way of illustration, not by way of limitation.

EXAMPLES

Example 1

ISOLATION AND CHARACTERIZATION OF ANCIENT BACILLUS ORGANISMS

Sample Source.

Structurally intact Dominican amber specimens containing fossilized stingless bees, *Problebeia dominicana*, and dating 25 to 40 million years old were used for extracting fossil tissues. These samples were rigorously authenticated, and all conditions under which the amber specimens were opened and fossil tissues extracted were sterilized to eliminate the possibility of contamination with modern microorganisms. All steps in the extraction process were conducted in a Class IIa laminar flow hood. In addition, various controls and mock extractions were conducted to verify the ancient status of any viable microorganism resulting, from the extractions.

Amber Sterilization And Cracking Procedures.

Amber specimens were surface sterilized by soaking overnight in 2% glutaraldehyde solution and rinsing three times with sterile deionized water (SDW). The rinsed pieces were then soaked in a 2% bleach solution for 5 minutes and rinsed twice in SDW. The amber was soaked for 30 minutes in 70% ethanol and flamed to complete the sterilization process. Sterile specimens were then cracked with liquid nitrogen as follows. The amber specimens were placed in sterile glass Petri dishes and covered with liquid nitrogen which was then allowed to evaporate. Hot, sterile, physiological saline was dripped over the amber pieces, causing the amber to crack along a plane that exposed the fossilized bee tissue as described, Cano et al., *Med. Sci. Res.* 20:249–251 (1992).

Fossil Extractions.

Using a sterile tuberculin syringe fitted with a sterile 27-gauge needle, small samples of fossilized bee tissue (thorax and the abdomen) were removed from the amber. Individual samples were suspended in individual vessels that contained TSB and incubated for two weeks at 35 degrees Centigrade to allow multiplication of any bacteria present. After this period, aliquots from vessels showing microbial growth were subcultured on solid media, Trypticase Soy Agar (TSA), to allow visualization and further isolation of distinct bacterial colonies.

Identification And Characterization Of Isolated Ancient Bacteria.

Identification of the ancient bacterial isolates was done by evaluating morphological and biochemical characteristics essentially as described, Gordon et al., The genus Bacillus, Department of Agriculture Handbook 427, Washington, D.C. (1973). All morphological and biochemical evaluations were conducted in a laminar flow hood. Enzymatic activities of the ancient Bacilli cultures were assessed using a semi-quantitative system that allows the detection of 19 enzymes (API ZYM Methodology, API Analytab Products). Enzymatic activity profiles of the BCA isolates were compared to those of extant *B. subtilis* obtained from the American type culture collection.

All ancient bacteria stock cultures were stored in secured and locked areas, and samples of all isolates were frozen and stored in a secured freezer at −70 degrees Centigrade.

Antimicrobial Activity Assays.

Ancient bacteria were tested for antimicrobial activity against various bacteria and fungi pathogenic to humans and plants using the cross-streak method (Colome et al., 1986). Ancient bacteria were streaked onto Mueller-Hinton agar and incubated at 35° C. for 24–48 hours. Pathogens were cross-streaked at 90 degree angles, and plates were incubated at 35° C. for bacterial pathogens and at room temperature for fungal pathogens. Cross-streaked plates were then monitored for growth inhibition 48 hours after cross-streaking, and for up to as long as two weeks thereafter.

Controls And Mock Extractions.

To further confirm that the ancient bacteria isolated were not modern contaminants picked up during the isolation process, several control experiments and mock extractions were conducted. In all extraction procedures, sentinel petri dishes were present to detect bacterial contaminants present in the hood, but none appeared.

Samples of the solutions used in the sterilization, cracking and fossil extraction procedures and pieces of the interior and exterior of the amber specimens were assayed for microbial contaminants by inoculating TSB and checking for microbial growth. No bacteria or fungi were detected in any of the solutions, or in the amber pieces. An assay for the presence of Bacillus DNA was conducted by inoculating 100 microliter samples of the solutions and small pieces of the amber specimen interior into Chelex solution, and extracting and PCR-amplifying Bacillus DNA using extant Bacillus-specific primers. Although some Bacillus DNA was detected in the solutions and on the surface of sterilized amber specimens, none was detected in samples taken from the interior of amber.

Another experiment was conducted to determine whether the sterilization process is effective at decontaminating amber specimens pretreated with live *Bacillus subtilis*. Briefly, amber specimens without fossil inclusions were submerged in endospore-containing *Bacillus subtilis* cultures overnight. Amber specimens were then sterilized as described above and exemplified below, and incubated in TSB under permissive conditions to allow for any contaminating bacterial growth. This control experiment was conducted eleven times, and in each case, no contamination was detected. Thus, the sterilization procedure is effective at eliminating the potential for modern-day bacterial contaminants on the surfaces of the amber specimens.

Mock extractions were conducted to assess potential environmental contamination of the samples during the extraction procedure. An amber specimen without fossil inclusions was surface-sterilized as described above and the extraction procedure described, infra, was simulated. Additionally, samples of the solutions and amber exterior and interior were tested for the presence of Bacillus endospores. Two mock extractions were conducted, and neither resulted in any bacterial growth.

Results.

Several ancient bacterial cultures were generated by inoculating bacterial growth media with samples of fossilized *Problebeia dominicana* thorax and abdomen tissues extracted from sterilized 25–40 million year old amber specimens as described infra. The morphological and biochemical characteristics of these isolates were evaluated, and indicated that all of the ancient bacteria were Bacillus or Bacillus-like organisms. Additionally, enzymatic activity profiles were determined. Morphology, biochemical characteristics, and enzymatic activity profiles for several modern Bacilli were also evaluated in parallel. The characteristics of modern and ancient Bacilli were then compared in order to more particularly define the taxonomy of these recovered ancient Bacilli.

The results of the morphological and biochemical evaluations are presented in Table I and Table II, respectively. Enzymatic profiles of the ancient bacteria are presented in Table III, and a comparison of ancient and modern/descendant bacteria is presented in Table IV.

TABLE I

| Sample ID | Gram Reaction | Size (um) | Shape of Endospore | Location of Endospore | Swelling Sporangia |
|---|---|---|---|---|---|
| BCA 1 | + | 0.75 × 3–4.5 | ellipsoidal | C | yes |
| BCA 2 | + | 1–1.25 × 2–5 | ellipsoidal | C | yes |
| BCA 3 | + | 0.75 × 2–2.5 | ellipsoidal | C | yes |
| BCA 5 | + | 0.75 × 2–5 | ellipsoidal | T | slight |
| BCA 6 | + | 0.75 × 2–3 | ellipsoidal | C | yes |
| BCA 7 | + | 0.75–1 × 4–13 | ellipsoidal | C, T | yes |
| BCA 8 | + | 1–1.4 × 4–13 | ellipsoidal | S, T | slight |
| BCA 12 | + | 0.5–0.75 × 3 | ellipsoidal | C, S, T | yes |
| BCA 13 | + | 0.75 × 2–4.5 | ellipsoidal | C | yes |
| BCA 15 | + | 1–1.25 × 4.5–6 | ellipsoidal | C, S, T | yes |
| BCA 16 | + | 0.75 × 3–4 | round | C | yes |
| BCA Ex 2 | + | 0.75 × 1–15 | round | C, S, T | yes |
| circ. 14175 | + | | ellipsoidal | S | yes |
| circ. 8241 | + | | ellipsoidal | C, S | yes |
| sub. 6051 | + | | ellipsoidal | C, S | no |
| lich 10716 | + | | ellipsoidal | C, S | slight |
| sph 4525 | + | | round | C | yes |

C = central
S = subterminal
T = terminal

TABLE II

| Sample ID | VP (pH) | Anaerobe | Arabinose A/G | Starch (Amylase) | Citrate | 50 C | 7% NaCl | pH 5.7 | Glucose A/G | Nitrate Reduced |
|---|---|---|---|---|---|---|---|---|---|---|
| BCA 1 | ¹+ (5) | − | ¹+/− | + | + | + | + | + | − | + |
| BCA 2 | ¹− (5) | − | ¹+/− | + | + | − | − | + | − | − |
| BCA 3 | ¹+ (5) | − | − | + | + | + | + | + | − | + |
| BCA 5 | ¹+ (5) | + | − | + | − | − | − | + | + | − |
| BCA 6 | ¹+ (5) | +/− | − | + | + | + | + | + | − | + |
| BCA 7 | ¹+ (5) | + | − | + | − | − | − | + | + | + |
| BCA 8 | ¹+ (5) | + | − | + | + | − | − | + | + | + |
| BCA 12 | ¹+ (5) | + | + | + | + | + | + | + | + | + |
| BCA 13 | ¹+ (5) | + | + | + | + | + | + | + | + | + |
| BCA 15 | ¹+ (5) | + | + | + | + | + | + | + | + | + |
| BCA 16 | ¹− (7) | − | +/− | − | − | − | − | − | +/− | |
| BCA Ex 2 | ¹− (7) | − | − | − | − | − | + | − | − | − |
| B. circ. 14175 | ¹− (6) | − | − | − | − | − | − | + | + | − |
| B. circ. 8241 | ¹− (5) | + | + | + | − | − | − | − | + | + |
| B. sub. 6051 | ¹+ (5) | + | − | + | + | − | − | + | | + |
| B. lich 10716 | ¹+ (5) | + | + | + | + | + | + | + | + | + |
| B. sph 4525 | ¹− (8) | − | − | − | + | − | − | − | − | − |

TABLE III

Table 5 API ZYM Test Results BCA Isolates
APIZYM RESULTS

| Test | Enzyme | BCA 1 Aug | BCA 3 Aug | BCA 5 Apr | BCA 5 Jul | BCA 6 Aug | BCA 7 Apr | BCA 7 Jul | BCA 8 Jul-93 |
|---|---|---|---|---|---|---|---|---|---|
| 1 | Cti | 0 | 0 | 0 | 0 | 0 | 0 | 0 | 0 |
| 2 | Alk Phos | 5 | 5 | 3 | 4 | 5 | 1 | 2 | 1 |
| 3 | Esterase | 3 | 3 | 1 | 3 | 3 | 2 | 2 | 2 |
| 4 | Ester, Lipase | 3 | 3 | 1 | 3 | 3 | 2 | 2 | 2 |
| 5 | Lipase | +/– | 1 | 0 | +/– | 0 | 0 | 1 | +/– |
| 6 | Leu, amn-pep | 0 | 0 | 0 | +/– | +/– | 4 | 5 | 5 |
| 7 | Val amn-pep | 0 | 0 | 0 | 0 | +/– | 0 | 3 | 1 |
| 8 | Cyt, amn-pep | 0 | 0 | 0 | 0 | 0 | 1 | 0 | 0 |
| 9 | Trypsin | 0 | 0 | 0 | 0 | +/– | 0 | 0 | 0 |
| 10 | Chymotrypsin | 0 | 0 | 0 | 1 | +/– | 0 | 0 | 0 |
| 11 | Acid Phos | 1 | 1 | 4 | 5 | +/– | 2 | 3 | 3 |
| 12 | Phosphohydro | 0 | 0 | 0 | 0 | 0 | 0 | 1 | 1 |
| 13 | a galactosidase | 0 | 0 | 0 | 0 | 0 | 0 | 0 | 0 |
| 14 | B galactosidase | 0 | 0 | 0 | 0 | 0 | 0 | 0 | 0 |
| 15 | B glucuronidase | 0 | 0 | 0 | 0 | 0 | 0 | 0 | 0 |
| 16 | a glucosidase | 0 | 0 | 1 | 0 | 0 | 0 | 0 | 0 |
| 17 | b glucosidase | 0 | 0 | 0 | 0 | 0 | 0 | 0 | 0 |
| 18 | N-ace, B glu | 0 | 0 | 0 | 0 | 0 | 0 | 0 | 0 |
| 19 | a mannosidase | 0 | 0 | 0 | 0 | 0 | 0 | 0 | 0 |
| 20 | a fucosidase | 0 | 0 | 0 | 0 | 0 | 0 | 0 | 0 |

| Test | Enzyme | BCA Apr | BCA Jul | BCA Aug | BCA Aug | BCA Jul | BCA Apr | BCA Jan |
|---|---|---|---|---|---|---|---|---|
| 1 | Cti | 0 | 0 | 1 | 1 | 0 | 0 | 0 |
| 2 | Alx Phos | 5 | 5 | 5+ | 5+ | 1 | 2 | 0 |
| 3 | Esterase | 3 | 2 | 3 | 2 | 3 | 2 | 3 |
| 4 | Ester, Lipase | 3 | 3 | 3 | 5 | 3 | 3 | 3 |
| 5 | Lipase | 0 | 1 | 2 | 1 | 0 | +/– | 0 |
| 6 | Leu, amn-pep | 3 | 4 | 3 | 2 | 1 | +/– | 0 |
| 7 | Val amn-pep | 0 | 1 | 1 | 0 | 0 | +/– | 0 |
| 8 | Cyt amn-pep | 0 | 0 | 0 | 0 | 0 | 0 | 0 |
| 9 | trypsin | 0 | 0 | 0 | 0 | 0 | +/– | 0 |
| 10 | Chymotrypsin | 0 | +/– | 0 | 0 | 1 | +/– | 0 |
| 11 | acid phos | 1 | 3 | 1 | 1 | +/– | +/– | 0 |
| 12 | Phosphohydro | 0 | +/– | +/– | 1 | 0 | 0 | 2 |
| 13 | a galactosidase | 0 | 0 | +/– | 0 | 0 | 0 | 5 |
| 14 | B galactosidase | 3 | 4 | 3 | 3 | 0 | 0 | 2 |
| 15 | B glucuronidase | 0 | 0 | 0 | 0 | 0 | 0 | 0 |
| 16 | a glucosidase | 3 | 3 | 1 | 1 | 0 | 0 | 0 |
| 17 | B glucosidase | 0 | 0 | 0 | 1 | 0 | 0 | 2 |
| 18 | N-ace, B Glu | 0 | 0 | 0 | 0 | 0 | 0 | 0 |
| 19 | a mannosidase | 0 | 0 | 0 | 0 | 0 | 0 | 0 |
| 20 | a fucosidase | 0 | 0 | 0 | 0 | 0 | 0 | 0 |

TABLE IV

Table 6, Comparison of Enzymatic Activity

| Test | Enzyme | B sub Apr-93 | B sub Jul-93 | BCA 1 Aug | BCA 3 Aug | BCA 6 Aug | B Aug-93 | BCA Ex Jul-93 | BCA Ex 2 Apr-93 | BCA 16 Jan-94 |
|---|---|---|---|---|---|---|---|---|---|---|
| 1 | Cti | 0 | 0 | 0 | 0 | 0 | 0 | 0 | 0 | 0 |
| 2 | Alk Phos | 1 | 1 | 5 | 5 | 5 | 0 | 1 | 2 | 0 |
| 3 | Esterase | 1 | 1 | 2 | 1 | 2 | 1 | 3 | 2 | 3 |
| 4 | Ester, | 1 | 3 | 3 | 3 | 3 | 3 | 3 | 3 | 3 |
| 5 | Lipase | 0 | 1 | +/– | 1 | 0 | 0 | 0 | +/– | 0 |
| 6 | Leu, amn-pep | 3 | 4 | 0 | 0 | +/– | 0 | 1 | +/– | 0 |
| 7 | Val amn-pep | 0 | 1 | 0 | 0 | +/– | 0 | 0 | +/– | 0 |
| 8 | Cyt, amn-pep | 0 | 0 | 0 | 0 | 0 | 0 | 0 | 0 | 0 |
| 9 | Trypsin | 0 | 0 | 0 | 0 | +/– | 0 | 0 | +/– | 0 |
| 10 | Chymotrypsin | 0 | 0 | 0 | 0 | +/– | 1 | 1 | +/– | 0 |
| 11 | Acid Phos | 1 | 2 | 1 | 1 | +/– | 0 | +/– | +/– | 0 |
| 12 | Phosphohydro | 0 | 0 | 0 | 0 | 0 | 0 | 0 | 0 | 2 |
| 13 | a | 0 | 0 | 0 | 0 | 0 | 0 | 0 | 0 | 3 |
| 14 | B | 0 | 0 | 0 | 0 | 0 | 0 | 0 | 0 | 2 |
| 15 | B | 0 | 0 | 0 | 0 | 0 | 0 | 0 | 0 | 0 |
| 16 | a | 1 | 3 | 0 | 0 | 0 | 0 | 0 | 0 | 0 |
| 17 | B | 0 | 0 | 0 | 0 | 0 | 0 | 0 | 0 | 2 |
| 18 | N-ace B glu | 0 | 0 | 0 | 0 | 0 | 0 | 0 | 0 | 0 |
| 19 | a | 0 | 0 | 0 | 0 | 0 | 0 | 0 | 0 | 0 |

TABLE IV-continued

Table 6, Comparison of Enzymatic Activity

| Test | Enzyme | B Aug-93 | B Jan-94 | BCA 5 Apr | BCA 5 Jul | BCA 7 Apr | BCA 7 Jul-93 | BCA 8 Jul-93 | Test # | Enzyme | B lich Apr-93 | B lich Jul-93 | BCA 13 Apr-93 | BCA 13 Jul-93 | BCA 12 Aug-93 | BCA 15 Aug-93 |
|---|---|---|---|---|---|---|---|---|---|---|---|---|---|---|---|---|
| 1 | Cti | 0 | 0 | 0 | 0 | 0 | 0 | 0 | 1 | Cti | 0 | 0 | 0 | 0 | 1 | 1 |
| 2 | Alk Phos | 3 | 3 | 3 | 4 | 1 | 2 | 1 | 2 | Alk Phos | 5 | 5 | 5 | 5 | 5+ | 5+ |
| 3 | Esterase | 1 | 3 | 1 | 3 | 2 | 1 | 1 | 3 | Esterase | 3 | 3 | 3 | 2 | 3 | 2 |
| 4 | Ester, | 1 | 4 | 1 | 3 | 2 | 2 | 2 | 4 | Ester, | 3 | 3 | 3 | 3 | 3 | 5 |
| 5 | Lipase | 0 | 1 | 0 | +/− | 0 | 1 | +/− | 5 | Lipase | 0 | 0 | 0 | 1 | 2 | 1 |
| 6 | Leu, amn-pep | 0 | 5 | 0 | +/− | 4 | 5 | 5 | 6 | Leu, amn-pep | 1 | 1 | 3 | 4 | 3 | 2 |
| 7 | Val amn-pep | 0 | 1 | 0 | 0 | 0 | 3 | 1 | 7 | Val amn-pep | 0 | 0 | 0 | 1 | 1 | 0 |
| 8 | Cyt, amn-pep | 0 | 1 | 0 | 0 | 1 | 0 | 0 | 8 | Cyt, amn-pep | 0 | 0 | 0 | 0 | 0 | 0 |
| 9 | Trypsin | 0 | 0 | 0 | 0 | 0 | 0 | 0 | 9 | Trypsin | 0 | 0 | 0 | 0 | 0 | 0 |
| 10 | Chymo-trypsin | 0 | 0 | 0 | 1 | 0 | 0 | 0 | 10 | Chymo-trypsin | 0 | 0 | 0 | +/− | 0 | 0 |
| 11 | Acid Phos | 5 | 5 | 4 | 5 | 2 | 3 | 3 | 11 | Acid Phos | +/− | 1 | 1 | 3 | 1 | 1 |
| 12 | Phospho-hydro | 1 | 2 | 0 | 0 | 0 | 1 | 1 | 12 | Phospho-hydro | 0 | 0 | 0 | +/− | +/− | 1 |
| 13 | a | 0 | 0 | 0 | 0 | 0 | 0 | 0 | 13 | a | 0 | 0 | 0 | 0 | +/− | 0 |
| 14 | B | 0 | 0 | 0 | 0 | 0 | 0 | 0 | 14 | B | +/− | 1 | 3 | 4 | 3 | 3 |
| 15 | a | 0 | 0 | 0 | 0 | 0 | 0 | 0 | 15 | B | 0 | 0 | 0 | 0 | 0 | 0 |
| 16 | a | 2 | 4 | 1 | 0 | 0 | 0 | 0 | 16 | a | 0 | 0 | 3 | 3 | 1 | 1 |
| 17 | B glucosidas | 0 | 0 | 0 | 0 | 0 | 0 | 0 | 17 | B | 0 | 0 | 0 | 0 | 0 | 1 |
| 18 | N-ace, B glu | 0 | 0 | 0 | 0 | 0 | 0 | 0 | 18 | N-ace, B glu | 0 | 0 | 0 | 0 | 0 | 0 |
| 19 | a | 0 | 0 | 0 | 0 | 0 | 0 | 0 | 19 | a | 0 | 0 | 0 | 0 | 0 | 0 |
| 20 | a fucosidase | 0 | no | 0 | 0 | 0 | 0 | 0 | 20 | a fucosidase | 0 | 0 | 0 | 0 | 0 | 0 |

Although the enzymatic profiles of the ancient bacteria correlated in several respects with those of modern Bacillus species, several differences were observed. For example, the ancient bacteria appeared to produce greater alkaline phosphatases and leucine aminopeptidase activities in relation to modern Bacilli. Also, modern *B. subtilis* and *B. cereus* produce α-glucosidase, whereas this activity was not detected in the ancient bacteria. In contrast, ancient *B. lichenformis*-like bacteria produced α-glucosidase, but the modern *B. lichenformis* did not. Moreover, ancient *B. lichenformis*-like bacteria appear to produce more β-galactosidase in relation to the modern *B. lichenformis* strain.

Based on these observations, applicants have identified the various ancient bacterial isolates by reference to their apparent closest extant Bacilli descendants. Accordingly, the following ancient bacteria are identified as tabulated below:

TABLE V

| | |
|---|---|
| BCA 1 | *B. subtilis*-like |
| BCA 2 | *B. megaterium*-like |
| BCA 3 | *B. subtilis*-like |
| BCA 5 | *B. cereus*-like |
| BCA 7 | *B. cereus*-like |
| BCA 8 | *B. cereus*-like |
| BCA 12 | *B. lichenformis*-like |
| BCA 13 | *B. lichenformis*-like |
| BCA 15 | *B. lichenformis*-like |
| BCA Ex 2 | *B. sphaericus*-like |
| BCA 16 | *B. sphaericus*-like |

Interestingly, it is known that *B. subtilis*, *B. megaterium*, *B. cereus*, *B. lichenformis*, and *B. sphaericus* all inhabit the digestive tracts of certain extant Hymenoptera bees.

The ancient Bacilli strains were also evaluated to the production of antimicrobial compounds using the cross-streak method described supra. Any significant amount of inhibition (i.e., no growth within at least 2 mm from the ancient bacteria streak) was scored as "partial inhibition" A score of "total inhibition" was only assigned if no growth was observed. The assays were performed twice, and only those ancient bacteria which reproducibly inhibited the growth of the test pathogen were scored as capable of either total or partial inhibition. The results are presented in Table VI.

TABLE VI

| Organism | Total Inhibition | Partial Inhibition |
|---|---|---|
| *Listeria monocytogenes* | | 1, 3, 6, 12, 13, 15 |
| *Salmonella pullorum* | | 1, 3, 6 |
| *Escherichia coli* | 12, 13, 15 | 1, 3, 6 |
| *Staphylococcus aureus* | 1 | 3, 6 |
| *Streptococcus pyogenes* | 1 | 3, 6, 13, 15 |
| *Shigella sonnei* | | 6 |
| *Agrobacter lumefaciens* | | 1, 3, 6, 12 |
| *Acinetobactor calcoaceticus* | 6, 12, 13, 15 | 1, 2, 3 |
| *Erwinia carotovora* | | 1, 3, 6 |
| *Verticillium dahliae* | | 1, 3 |
| *Penicillium notatum* | | 1, 3, 6 |

*Test performed once only

Example 2

DECONTAMINATION OF AMBER SPECIES

Eleven (11) pieces of amber (without inclusions) are surface sterilized and cracked in a Trypticase Soy Agar (BBL, Cockeysville, Md.) endosporulating culture of *Bacillus subtilis* according the procedure described above. Specifically, the amber was: (1) weighed in a tared weighing boat; (2) immersed in 2% buffered glutaraldehyde at 35° C. for at least 12 hours in vacuo; (3) rinsed three times in approximately 250 ml of sterile, double distilled water (SDDW) and culture rinse water on TSB to evaluate the effectiveness of the sterilization procedure; (4) immersed in 10% bleach for an additional 6 hours at 37° C.; (5) rinsed three times in SDDW and culture rinse water on TSB to evaluate the effectiveness of the sterilization procedure; (6) immersed in 70% ethanol for two (2) hours at 35° C. and (7) exposed to flames to evaporate the alcohol.

The number of endospores was estimated (by direct count) to be about $1.6 \times 10^7$ endospores/ml of TSB. The amber was allowed to soak overnight in the culture before carrying out the sterilization procedure. Tube containing 10 ml TSB were inoculated with the surface sterilized amber and incubated at 35° C. for 14 days. No bacterial growth was detected in any of the eleven TSB tubes after a two week incubation period.

Example 3

EXTRACTION OF ANCIENT MICROORGANISMS FROM VARIOUS SOURCES OF AMBER (Pulverizing Method)

Isolation Of *Bacillus subtilis*-Like Microorganism From German Amber.

A German amber (bitterfelder) specimen (15–25 million-years-old), containing soil and insect debris was surface-sterilized and the tissue harvested using the sterilization and pulverizing extraction methods described above. Cream-colored, mucoid, colonies were seen on the surface of TSA agar after 4 days of incubation at 30° C. The isolate was coded AG-14-BF-2. Microscopic examination revealed Gram positive rods, <1.0 μm in diameter with oval spores, not swelling the sporangium. The Bacillus sp. was strictly aerobic, catalase positive, Voges-Proskauer positive, pH of V-P broth <6, hydrolyzed casein, gelatin, and starch. The isolate was presumptively identified as *Bacillus subtilis*-like.

The API-ZYM profile was as follows: Alkaline phosphatase (+), Butyrate esterase (+/–), Caprylate esterase (+), Myristate lipase (–), Leucine aminopeptidase (–), Valine aminopeptidase (–), Cystine aminopeptidase (–), Trypsin (–), Chymotrypsin (–), Acid phosphatase (–), Phosphoamidase (–), α-galactosidase (–), β-galactosidase (–), β-glucoronidase (–), α-glucosidase (–), β-glucosidase (–), N-acetyl-β-glucosamidase (–), α-mannosidase (–), β-fucosidase (–)

Isolation Of Actinomyces sp.-Like Microorganism From Washington State Calmount Amber.

A Washington State Calmount amber specimen (38–54 million-years-old), containing soil particles was surface-sterilized and the tissue harvested using the sterilization and pulverizing extraction methods described above. Whitish, powdery colonies appeared on the surface of Czapek agar plates with 4% yeast extract after 8 days of incubation at 30° C. The isolate was coded AG-16-WA-3.Microscopic examination revealed the presence of Gram positive, branching filaments and short rods. The isolate was facultatively anaerobic and grew well in starch-casein agar, producing dry, powdery colonies measuring 1.0–2.5 mm in diameter after 7 days of growth. The isolate was shown to produce an alkaline protease as determined by the digestion of casein in SMA agar plates with the pH adjusted to 8.1. The isolate was presumptively identified as Actinomyces sp.

Isolation Of *Bacillus sphaericus*-Like Microorganism From Chinese Amber.

A Chinese amber specimen (40–53 million-years-old), containing soil particles was surface-sterilized and the tissue harvested using the sterilization and pulverizing extraction methods described above. Whitish, pasty colonies were seen on the surface of TSA agar after 5 days of incubation at 30° C. The isolate was coded AG-17-CH-1. Microscopic examination revealed Gram positive rods, <1.0 μm in diameter with round spores, swelling the sporangium. The Bacillus sp. was facultatively anaerobic, catalase positive, Voges-Proskauer negative, pH of V-P broth >7, hydrolyzed casein, gelatin, and starch. The isolate was presumptively identified as *Bacillus sphaericus*-like.

The API-ZYM profile was as follows: Alkaline phosphatase (–), Butyrate esterase (–), Caprylate esterase (+), Myristate lipase (–), Leucine aminopeptidase (–), Valine aminopeptidase (–), Cystine aminopeptidase (–), Trypsin (–), Chymotrypsin (+), Acid phosphatase (–), Phosphoamidase (–), α-galactosidase (–), β-galactosidase (–), β-glucoronidase (–), α-glucosidase (–), β-glucosidase (–), N-acetyl-β-glucosamidase (–), α-mannosidase (–), β-fucosidase (–).

Isolation Of *Arthrobacter aurescens*-Like Microorganism From Dominican Amber.

A Dominican amber specimen (25–40 million-years-old), containing leaves and flowers of the extinct legume *Hymenaea protera* was surface-sterilized and tissue harvested using the sterilization and pulverizing extraction methods described above. Yellow, pasty colonies were seen on the surface of TSA agar after 7 days of incubation at 30° C. The isolate was coded AMG7. Microscopic examination revealed Gram positive, motile, pleomorphic rods with definite tendency toward a rod-coccus cycle. No mycelium was produced and were strict aerobes. The isolate was presumptively identified as *Arthrobacter aurescens*-like based on the presence of the yellow pigment and the ability to hydrolyze starch. This organism was shown to inhibit the growth of *Staphylococcus aureus* and *Escherichia coli* in cross-streak assays.

Isolation Of *Bacillus subtilis*-Like Microorganism From Lebanese Amber.

A Lebanese amber specimen (120–135 million-years-old), containing soil particles was surface-sterilized and the tissue harvested using sterilization and pulverizing extraction methods described above. Cream-colored, mucoid, colonies were seen on the surface of TSA agar after 5 days of incubation at 30° C. The isolate was coded AG-14-LA-1. Microscopic examination revealed Gram positive rods, <1.0 μm in diameter with oval spores, not swelling the sporangium. The Bacillus sp. was strictly aerobic, catalase positive, Voges-Proskauer positive, pH of V-P broth <6, hydrolyzed casein, gelatin, and starch. The isolate was presumptively identified as *Bacillus subtilis*-like. Additionally, this organism was shown to produce an alkaline protease that was both stable at 65° C. and active at pH 8.1.

The API-ZYM profile was as follows: Alkaline phosphatase (+), Butyrate esterase (+), Caprylate esterase (+), Myristate lipase (–), Leucine aminopeptidase (–), Valine aminopeptidase (–), Cystine aminopeptidase (–), Trypsin (–), Chymotrypsin (–), Acid phosphatase (–), Phosphoamidase (–), α-galactosidase (–), β-galactosidase (+), β-glucoronidase (–), α-glucosidase (–), β-glucosidase (–), N-acetyl-β-glucosamidase (–), α-mannosidase (–), β-fucosidase (–).

Isolation Of Streptomyces sp.-Like Microorganism From Baltic Amber.

A Baltic amber specimen (40 million-years-old), containing soil particles and plant debris was surface-sterilized and the tissue harvested using the sterilization and pulverizing extraction method described above. Grayish, powdery colonies with aerial mycelium appeared on the surface of Czapek agar plates with 4% yeast extract after 7 days of incubation at 30° C. The isolate was coded AG-11-BA-11. Microscopic examination revealed the presence of Gram positive, branching filaments with sporangia producing spores in chains and short rods. The isolate was shown to produce a protease as determined by the digestion of casein in SMA agar plates. The isolate was presumptively identified as Streptomyces sp.

Isolation Of Saccharomyces sp.-Like Microorganism From Dominican Amber.

A Dominican amber specimen (40 million-years-old), containing soil particles and insect excrements was surface-sterilized and the tissue harvested using the above-described sterilization and pulverizing methods. White, creamy colonies appeared on the surface of PDA agar after 7 days incubation at 30° C. The isolated was coded AG-11-DM-6. Microscopic examination revealed round to oval, budding yeast cells, measuring 5.0 to 7.5 μm in diameter. The organism was not encapsulated, did not form pseudohyphae on Levine's EMB agar (Difco), and fermented glucose, sucrose, lactose, and galactose with the production of $CO_2$ (gas) and ethanol (alcohol). The isolate was presumptively identified as Saccharomyces sp.

*Micrococcus roseus*-Like Microorganism From Columbian Copal. A Colombian copal specimen (approximately 2 million-years-old) containing soil particles and insect excrements was surface-sterilized and tissue harvested using the sterilization and pulverizing extraction methods described above. Red, pasty colonies appeared on the surface of TSA agar after 5 days incubation at 30° C. The isolated was coded AG-11-CC-5. Microscopic examination revealed Gram-positive cocci arranged in pairs, tetrads, and irregular packets. The isolate produced acid glucose but not from glycerol and hydrolyzed starch. The isolate was presumptively identified as *Micrococcus roseus*-like.

Isolation Of Penicillium-Like Organism From Baltic Amber.

Baltic amber (Lithuanian) specimen (40 million-years-old) containing soil particles was surface-sterilized and tissue harvested using the sterilization and pulverizing extraction methods described above. Powdery, grayish-green colonies with a yellowish, membranous reverse and no diffusible pigment appeared on the surface of PDA and Czapek agars after 7 days of incubation at 30° C. The isolated was coded AG-11-BA-5. Microscopic examination of lactophenol cotton blue (LPB) wet mounts revealed hyline, septate hyphae with phialidic conidiogenous cells in penicillia. Phialoconidia were in chains with smooth or echinulate outer walls. The isolate was presumptively identified as Penicillium sp. Cross-streak assays revealed the presence of growth-inhibitory substances for *Staphylococcus aureus, Streptococcus pyogenes,* and *Escherichia coli.* Colonies digested casein when grown on SMA.

Isolation Of Actinomyces Sp.-Like Microorganism From African Copal.

An African copal specimen (approximately 5,000 years-old), containing soil particles and insect debris was surface-sterilized and tissue harvested using the sterilization and pulverizing extraction methods described above. Whitish, powdery colonies appeared on the surface of Czapek agar plates with 4% yeast extract after 7 days of incubation at 30° C. The isolate was coded AG-11-AC-14. Microscopic examination revealed the presence of Gram positive, branching filaments and short rods. The isolate was facultatively anaerobic and grew well in starch-casein agar, producing white, dry, powdery colonies measuring 1.5–2.5 mm in diameter after 7 days of growth. The isolate was shown to produce a protease as determined by the digestion of casein in SMA agar plates. The isolate was presumptively identified as Actinomyces sp.

Isolation Of A Coryneform Thermophile-Like Microorganism From Burmese Amber.

A Burmese amber specimen (38–54 million-years-old), containing soil particles was surface-sterilized as described above and the tissue harvested using the pulverizing extraction method, also described above. Yellowish, pasty colonies appeared on the surface of TSA plates after 7 days of incubation at 55° C. The isolate was coded AG-12-BM-2. Microscopic examination revealed the presence of Gram positive rods, arranged in chains, palisades, and picket-fence-like patterns. The isolate was facultatively anaerobic and grew well in starch-casein agar. The isolate was shown to produce a protease as determined by the digestion of casein in SMA agar plates. The isolate was tentatively identified as a coryneform thermophile.

Isolation Of Bacillus Sp.-Like Microorganism From Columbian Copal.

A Colombian copal specimen (approximately 2 million-years-old), containing soil particles was surface-sterilized and tissue harvested using sterilization and pulverizing extraction methods described above. Cream-colored, flaky, colonies were seen on the surface of TSA agar after 5 days of incubation at 55° C. The isolate was coded AG-13-CC-33. Microscopic examination revealed Gram positive rods, >1.0 μm in diameter with oval spores swelling the sporangium. The *Bacillus sp.* was strictly aerobic, catalase positive, Voges-Proskauer positive, pH of V-P broth <6, hydrolyzed casein, gelatin, and starch. The isolate was presumptively identified as Bacillus sp. Additionally, this organism was shown to produce an alkaline protease that was both stable at 65° C. and active at pH 8.1.

The API-ZYM profile was as follows: Alkaline phosphatase (+), Butyrate esterase (+), Caprylate esterase (+), Myristate lipase (−), Leucine aminopeptidase (−), Valine aminopeptidase (−), Cystine aminopeptidase (−), Trypsin (−), Chymotrypsin (+), Acid phosphatase (−), Phosphoamidase (−), α-galactosidase (−), β-galactosidase (−), β-glucoronidase (−), α-glucosidase (−), β-glucosidase (−), N-acetyl-β-glucosamidase (−), α-mannosidase (+), β-fucosidase (−).

Isolation Of *Proteolytic Coccobacillus*-Like Microorganism From Japanese Amber.

A Japanese amber specimen (approximately 80 million-years-old), containing soil particles was surface-sterilized and the tissue harvested using the sterilization and pulverizing extraction methods described above. Whitish, mucoid colonies were seen on the surface of TSA agar after 5 days of incubation at 30° C. The isolate was coded AG-19-JA-2. Microscopic examination revealed Gram positive coccobacilli, >1.0 μm in diameter with oval spores swelling the sporangium. The Bacillus sp. was facultatively aerobic, catalase positive, oxidase and hydrolyzed casein and gelatin, but not starch. The isolate was tentatively identified as a Gram positive, proteolytic coccobacillus.

Isolation Of Streptomyces sp.-Like Microorganism From Washington State Amber.

A Washington State amber specimen (38–54 million-years-old), containing soil particles and plant debris was surface-sterilized as described in above and the tissue harvested using the pulverizing extraction method. Grayish, powdery colonies with aerial mycelium appeared on the surface of Czapek agar plates with 5% yeast extract after 7 days of incubation at 30° C. The cultures had a characteristic musty odor of streptomycetes. The isolate was coded AG-15-WA-18. Microscopic examination revealed the presence of Gram positive, branching filaments with sporangia producing spores in chains and short rods. The isolate was shown to produce an antimicrobial agent that inhibited both Gram positive and Gram negative bacteria, including, *Staphylococcus aureus, Bacillus subtilis,* and *Escherichia coli.* The isolate was presumptively identified as Streptomyces sp-like.

Isolation Of Cladosporium sp.-Like Microorganism From Lebanese Amber.

A Lebanese amber specimen (120–135 million-years-old) containing soil particles was surface-sterilized as described above and the tissue harvested using the pulverizing extraction method, also described above. Powdery, olive-drab colored colonies with a dark, membranous reverse and no diffusible pigment appeared on the surface of Czapek agar after 10 days of incubation at 25° C. The isolate was coded AG-13-LA-5. Microscopic examination of lactophenol cotton blue (LPB) wet mounts revealed dematiaceous, septate hyphae with oval, dematiaceous, blastoconidia with dysjunctors. Branching was evident from shield cells. The isolate was presumptively identified as Cladosporium sp.-like. Colonies digested chitin when grown on SMA and assimilated a variety of carbohydrates, including glucose and sucrose.

Example 4

EXTRACTION OF ANCIENT MICROORGANISMS FROM VARIOUS SOURCES OF AMBER (Cracking Method)

Isolation Of Bacillus Sp.-Like Microorganism From Burmese Amber.

A Burmese amber specimen (38–54 million-years-old), containing an insect and pollen grains was surface-sterilized and the tissue harvested using sterilization and cracking extraction methods described above. Cream-colored, mucoid, colonies were seen on the surface of TSA agar after 6 days of incubation at 30° C. The isolate was coded AG-15-BM-1. Microscopic examination revealed Gram positive rods, >1.0 μm in diameter with oval spores, not swelling the sporangium. The Bacillus sp. was facultatively anaerobic, acidotolerant, catalase positive, Voges-Proskauer positive, pH of V-P broth <6, hydrolyzed casein, gelatin, and starch, utilized citrate as the sole source of carbon The isolate was presumptively identified as *Bacillus cereus*-like.

The API-ZYM profile was as follows: Alkaline phosphatase (+), Butyrate esterase (+), Caprylate esterase (+), Myristate lipase (–), Leucine aminopeptidase (+), Valine aminopeptidase (–), Cystine aminopeptidase (–), Trypsin (–), Chymotrypsin (+), Acid phosphatase (+), Phosphoamidase (–), α-galactosidase (–), β-galactosidase (–), β-glucoronidase (+), α-glucosidase (–), β-glucosidase (–), N-acetyl-β-glucosamidase (–), α-mannosidase (–), β-fucosidase (–).

Isolation Of Bacillus Sp.-Like Microorganism From Canadian Amber.

A Canadian amber specimen (68–75 million-years-old), containing insect parts was surface-sterilized and the tissue harvested using the sterilization and cracking extraction method described above. Cream-colored, pasty, colonies were seen on the surface of TSA agar after 5 days of incubation at 30° C. The isolate was coded AG-18-CA-2. Microscopic examination revealed Gram positive rods, >1.0 μm in diameter with oval spores swelling the sporangium. The Bacillus sp. was facultatively aerobic, catalase positive, Voges-Proskauer negative, pH of V-P broth >7, hydrolyzed casein and gelatin, but not starch. The isolate was presumptively identified as Bacillus sp.

Example 5

EXTRACTION OF ANCIENT MICROORGANISMS FROM VARIOUS SOURCES OF AMBER (Flushing Method)

Isolation Of Pseudomonas Sp.-Like Organism From Dominican Amber.

A Dominican amber specimen (25–40 million-years-old), containing water droplets (some with soil particles therein) was surface-sterilized and the tissue harvested using the sterilization and flushing extraction methods described above. Yellowish, moist, glistening colonies were seen on the surface of TSA agar after 5 days of incubation at 30° C. The isolate was coded AG-10-DA-1. Microscopic examination revealed Gram negative, motile rods. The isolate was aerobic, reduced nitrate, catalase positive, oxidase positive, hydrolyzed casein and gelatin, but not starch. The isolate was presumptively identified as Pseudomonas sp.

Example 6

EXTRACTION OF ANCIENT MICROORGANISMS FROM VARIOUS SOURCES OF AMBER (Drilling Method)

Isolation Of *Bacillus pumilus*-Like Organism From Mexican Amber.

A Mexican amber specimen (20–35 million-years-old), containing an inclusion of Plebeia silaceae was surface-sterilized and the tissue harvested using sterilization and drilling extraction methods described above. Buff, creamy colonies were seen on the surface of TSA agar after 4 days of incubation at 25° C. The isolate was coded AG-12-MX-2. Microscopic examination revealed Gram positive rods, <1.0 μm in diameter with oval spores, not swelling the sporangium. The Bacillus sp. was strictly aerobic, catalase positive, Voges-Proskauer positive, pH of V-P broth <6, hydrolyzed casein and gelatin but not starch. The isolate was presumptively identified as *Bacillus pumilus*-like.

The API-ZYM profile was as follows: Alkaline phosphatase (–), Butyrate esterase (–), Caprylate esterase (+), Myristate lipase (–), Leucine aminopeptidase (–), Valine aminopeptidase (–), Cystine aminopeptidase (–), Trypsin (–), Chymotrypsin (–), Acid phosphatase (–), Phosphoamidase (–), α-galactosidase (–), β-galactosidase (–), β-glucoronidase (–), α-glucosidase (–), β-glucosidase (–), N-acetyl-β-glucosamidase (–), α-mannosidase (–), β-fucosidase (–).

Example 7

VALIDATION BY NUCLEIC ACID SEQUENCE ANALYSIS

DNA extracted from the putative ancient isolate BCA16 (identified as *Bacillus sphaericus*) was used as templates using the primer pair BCF1 (CGGGAGGCAGCAGTAGG-GAAT) and BCR2 (CTCCCCAGGCGGAGTGCTTAAT). These primers were obtained from the 16s rRNA sequence of *B. circulans* (GenBank Accession Number X60613) and amplify a 530 base pair region of this gene. DNA was extracted using a silica gel suspension as described by Cano and Poinar, Cano, R. J. & Poinar, H. N., Biotechniques 15:8–11 (1993). For PCR amplification, 5 µl of extracted DNA was used as the source of DNA for enzymatic amplification by PCR. Symmetric PCR amplifications were performed using 2 units of low DNA AmpliTaq DNA polymerase (Perkin-Elmer, Norwalk, Conn.), 2 µg/ml bovine serum albumin, 0.5 µM each of BCA341F and BCA871R primers, 2.0 mM $MgCl_2$, and 0.2 mM deoxynucleotide triphosphates in a total volume of 50 µl. All reagent mixtures and sample dilutions were performed in an ice water bath and the tubes placed in the thermal cycler after the heat block reached 80° C. Polymerase chain reactions were performed using a Temp-Tronic® thermal cycler dry bath (Thermolyne, Dubuque, Iowa). During the first cycle the DNA templates were denatured for 2 min at 95° C. followed by a primer annealing step at 58° C. for 1 min, and an extension step of 1 min at 72° C. The following 30 cycles consisted of a 1 min denaturation step at 94° C., a 1 min primer annealing step at 58° C., and a 1 min primer extension step at 72° C. The last cycle consisted of a 1 min denaturation step, a 1 min primer annealing step, and a 10 min primer extension step. The products of each amplification were evaluated by 1.2% agarose in Tris-Acetate-EDTA buffer. Amplification products were cloned using a TA Cloning® kit (Invitrogen, San Diego, Calif.) as per manufacturer's instructions. Cloned plasmid DNA was sequenced using a Sequenase II DNA sequencing kit (USB, Cleveland, Ohio) with α-thio $^{35}$S-dATP as per manufacturer's instructions. Three clones were sequenced for each sample, using both SP6 and T7 sequencing primers. Electrophoresis of sequencing products was performed in a 6% sequencing gel (GEL-MIX 6 Gibco BRL, Gaithersburg, Md.). Autoradiographs of air-dried sequencing gels were made using XAR X-ray film (Kodak, Rochester, Minn.). Sequences were scanned into a Sparc10 station (Sun Microsystems, Mountain View, Calif.) and analyzed using the BioImage DNA analysis software (Millipore, Bedford, Mass.). Autoradiographs were evaluated manually to verify the computer-analyzed sequences. Sequences were aligned manually using the Genetic Data Environment (GDE 2.1) text editor. The 16S rDNA nucleotide sequences of BCA16, the rate of nucleotide substitution, r, is calculated by dividing the number of substitutions between the putative ancient *B. sphaericus* and extant *B. sphaericus* by the number of nucleotide sites analyzed. This number, K, is then divided by 2T, where T is the time of divergence between the two sequences, Li, Wen-Hsiung, & Dan Grauer, *Fundamentals of Molecular Evolution*, Sinauer Associates, Inc., Sunderland, Mass. (1991). The time of divergence (T), also the age of the amber piece, can be calculated by dividing K/n2R where n is the number of nucleotides analyzed (487), and r is $0.3$–$04 \times 10^{-9}$ substitutions per position per year. The number of nucleotide substitutions between BCA16 and the extant *B. sphaericus* was 13. Based on this K value, T is $33.3 \times 10^6$ years to $44.4 \times 10^6$ years. As the age of Dominican amber mines is between 25 and 40 million years, the rate of nucleotide substitutions between the putative ancient *B. sphaericus* and the extant one is consistent with the age of the amber, and therefore the results validate the claim that BCA16 was an ancient isolate of *B. spahericus* in Dominican amber.

Example 8

VALIDATION OF ANTIQUITY OF ISOLATES BY NUCLEOTIDE SEQUENCE ANALYSIS

DNA is extracted from putative ancient isolates and a segment of the 16S rRNA gene or the rbcL gene (for photosynthetic organisms) amplified using appropriate primers. PCR amplifications are performed using 1 unit of low-DNA Taq polymerase (AmpliTaq-LD DNA polymerase, Perkin Elmer, Norwalk, Conn.), 2.5 g/ml bovine serum albumin fraction V (Sigma, St. Louis, Mo.), 0.5 5M each of the primers, 2.0 mM $MgCl_2$, and 0.2 mM deoxynucleotide triphosphates (dNTPs) in a total volume of 50 1. All reagent mixtures and sample dilutions are performed in an ice water bath and the tubes placed in the thermal cycler after the heat block reached 80° C. Polymerase chain reactions are performed using a thermal cycler dry bath with the appropriate protocol (optimized using the appropriate template DNA and primers). PCR products are cloned into suitable cloning vectors and then sequenced using standard protocols. Sequences are aligned either manually or with the aid of an alignment software package and the sequences evaluated. The rate of nucleotide substitution for 16S rRNA genes, r, is assumed to be $0.3$–$0.4 \times 10^{-9}$ substitutions per position per year based on previous reports, Ochman and Wilson, *J. Mol. Evol.* 26:74–86 (1987); Moran, et al., *Proc. R. Soc. Lond. B.* 253:167–171 (1993), and $1.9 \times 10^{-9}$ for the rbcL gene for various plant taxa Zurawski and Clegg, Zurawski and Clegg, *Annual Review Plant Physiology* 38:391–418 (1987). The time of divergence between the two taxa (the age of the amber from which the putative ancient microorganisms was isolated) is determined by dividing the number of substitutions between the putative ancient organism and its closest extant relative by 2 r times the number of nucleotides analyzed. The time of divergence between the two taxa should be roughly the same as the age of the amber from which the isolate was obtained.

MICROORGANISM DEPOSITS

Cultures of the following ancient bacteria were deposited with the NRRL, Peoria, Ill., on Jan. 28, 1994 (BCA cultures) and Nov. 1, 1994 (AG cultures), however, AG culture deposits NRRL Y-21355 NRRL 21356 were deposited on Nov. 16, 1994 and Jan. 4, 1995, respectively and each of the cultures have been assigned the following, accession numbers:

| CULTURE | TYPE | ACCESSION NUMBER |
| --- | --- | --- |
| BCA 1 | *B. Subtilis*-like | B-21177 |
| BCA 3 | *B. Subtilis*-like | B-21178 |
| BCA 5 | *B. cereus*-like | B-21179 |
| BCA 7 | *B. cereus*-like | B-21180 |
| BCA 13 | *B. lichenformis*-like | B-21181 |
| BCA 15 | *B. lichenformis*-like | B-21182 |
| BCA Ex 2 | *B. Sphaericus*-like | B-21184 |
| BCA 16 | *B. Sphaericus*-like | B-21183 |
| AG-10-DA-1 | Pseudomonas-like | |
| AG-11-DM-6 | Saccharomyces-like | |

-continued

| CULTURE | TYPE | ACCESSION NUMBER |
|---|---|---|
| AG-13-LA-5 | Cladosporium-like | |
| AG-15-WA-19 | Streptomyces-like | |
| AG-11-AC-14 | Actinomyces-like | |
| AG-11-BA-5 | Penicillum-like | |

The present invention is not to be limited in scope by the bacteria cultures deposited or the embodiments disclosed herein, which are intended as single illustrations of one aspect of the invention, and any which are functionally equivalent are within the scope of the invention. Indeed, various modifications of the invention, in addition to those shown and described herein, will become apparent to those skilled in the art from the foregoing description. Such modifications are intended to fall within the scope of the appended claims. All patents, patent applications, and publications mentioned herein are hereby incorporated by reference.

What is claimed is:

1. An isolated, viable culture of a microorganism obtained from within a naturally occurring resin selected from the group consisting of amber and copal by sterilizing such resin, extracting the microorganism from said resin, reviving said microorganism to a viable state, and culturing said extracted microorganism.

2. The culture of claim 1 wherein the naturally-occurring resin is selected from the group consisting of Lebanese amber, Washington State amber, Mexican amber, Canadian amber, Japanese amber, Baltic amber, German amber, Colombian copal, Burmese amber, Dominican amber, Chinese amber and African copal.

3. The culture of claim 1 wherein the naturally-occurring resin is surface-sterilized.

4. The culture of claim 1 wherein the microorganism is extracted from a naturally-occurring resin by a pulverizing extraction method.

5. The culture of claim 1 wherein the resin is prepared with liquid nitrogen prior to pulverization.

6. The culture of claim 1 wherein the resin is frozen to between about −20° C. and about −140° C. prior to pulverization.

7. The culture of claim 6 wherein the resin is frozen to about −80° C.

8. The culture of claim 1 wherein the microorganism is extracted from a naturally-occurring resin by a cracking extraction method.

9. The culture of claim 1 wherein the microorganism is extracted from a naturally-occurring resin by a drilling extraction method.

10. The culture of claim 1 wherein the microorganism is extracted from a naturally-occurring resin by a flushing extraction method.

11. The culture of claim 1 wherein the microorganism is contained in insect material fossilized within the resin.

12. The culture of claim 11 wherein the insect material is selected from the group consisting of insect tissue, insect feces and insect nest.

13. The culture of claim 1 wherein the microorganism is contained in plant material fossilized within the resin.

14. The culture of claim 13 wherein the plant material is selected from the group consisting of roots, leaves, seeds, twigs, bark, plant tissue, spores, pollen, flowers, grasses, ferns and legumes.

15. The culture of claim 1 wherein the microorganism is contained in soil fossilized within the resin.

16. The culture of claim 1 wherein the microorganism is contained in water fossilized within the resin.

17. The culture of claim 1 wherein the age of the microorganism is determined by nucleic acid analysis.

18. The culture of claim 1 wherein the microorganism is selected from the group consisting of bacteria, fungi, virus, protozoa, microalgae, arthropod and nematode.

19. A method for obtaining an isolated, viable culture of a microorganism from within a naturally-occurring resin selected from the group consisting of amber and copal, comprising the steps: (a) sterilizing the surface of the naturally-occurring resin; (b) extracting said microorganism from the naturally-occurring resin; (e) reviving said microorganism to a viable state, and (d) culturing said extracted and revived microorganism.

20. The method of claim 19 wherein the naturally-occurring resin is selected from the group consisting of Lebanese amber, Washington State amber, Mexican amber, Canadian amber, Japanese amber, Baltic amber, German amber, Columbian copal, Burmese amber, Dominican amber, Chinese amber and African copal.

21. The method of claim 19 wherein the microorganism is extracted from the naturally-occurring resin by a pulverizing extraction method.

22. The method of claim 21 wherein the resin is prepared with liquid nitrogen prior to pulverization.

23. The culture of claim 21 wherein the resin is frozen to between about −20° C. and about −140° C. prior to pulverization.

24. The culture of claim 23 wherein the resin is frozen to about −80° C.

25. The method of claim 19 wherein the microorganism is extracted from the naturally-occurring resin by a cracking extraction method.

26. The method of claim 19 wherein the microorganism is extracted from the naturally-occurring resin by a drilling extraction method.

27. The method of claim 19 wherein the microorganism is extracted from the naturally-occurring resin by a flushing extraction method.

28. The method of claim 19 wherein the microorganism is contained in insect material fossilized within the resin.

29. The method of claim 28 wherein the insect material is selected from the group consisting of insect tissue, insect feces, and insect nest.

30. The method of claim 19 wherein the microorganism is contained in plant material fossilized within the resin.

31. The method of claim 30 wherein the plant material is selected from the group consisting of roots, leaves, seeds, twigs, bark, plant tissue, spores, pollen, flowers, grasses, ferns and legumes.

32. The method of claim 19 wherein the microorganism is contained in soil fossilized within the resin.

33. The method of claim 19 wherein the microorganism is contained in water fossilized within the resin.

34. The method of claim 19 wherein the age of the microorganism is determined by nucleic acid analysis.

35. The method of claim 19 wherein the microorganism is selected from the group consisting of bacteria, fungi, virus, protozoa, microalgae, arthropod and nematode.

36. An isolated biologically pure and viable culture of a microorganism isolated from within a naturally-occurring resin selected from the group consisting of amber and copal.

37. The culture of claim 36 wherein the microorganism is selected from the group consisting of bacteria, fungus, virus, plant, protozoa, microalgae, arthropod and nematode.

38. The culture of a microorganism according to claim 36 wherein the microorganism is isolated from insect material fossilized within a resin.

39. The culture of a microorganism according to claim 36 wherein the microorganism is isolated from soil fossilized within a resin.

40. The culture of a microorganism according to claim 36 wherein the microorganism is isolated from plant material fossilized within a resin.

41. The culture of a microorganism according to claim 36 wherein the microorganism is isolated from water fossilized within a resin.

42. An isolated, biologically pure and viable microorganism selected from the group consisting of: ancient Bacillus strain BCA 1 as deposited with the NRRL and assigned accession number B-21177, ancient Bacillus strain BCA 3 as deposited with the NRRL and assigned accession number B-21178, ancient Bacillus strain BCA 5 as deposited with the NRRL and assigned accession number B-21179, ancient Bacillus strain BCA 7 as deposited with the NRRL and assigned accession number B-21180, ancient Bacillus strain BCA 13 as deposited with the NRRL and assigned accession number B-21181, ancient Bacillus strain BCA 15 as deposited with the NRRL and assigned accession number B-21182, ancient Bacillus strain BCA Ex 2 as deposited with the NRRL and assigned accession number B-21184, ancient Bacillus strain BCA 16 as deposited with the NRRL and assigned accession number B-21183, ancient Pseudomonas strain AG-10-DA-1 as deposited with the NRRL and assigned accession number B-21357, ancient Saccharomyces strain AG-11-DM-6 as deposited with the NRRL and assigned accession number Y-21355, ancient Actinomyces strain AG-11-AC-14 as deposited with the NRRL and assigned accession number 21356, ancient Penicillium strain AG-11-BA-5 as deposited with the NRRL and assigned accession number 21354, ancient Cladosporium strain AG-13-LA-5 as deposited with the NRRL and assigned accession number 21353 and ancient Streptomyces strain AG-15-WA-19 as deposited with the NRRL and assigned accession number 21352.

43. An isolated biologically pure ancient microorganism that has been recovered from within a naturally occurring resin selected from the group consisting of amber and copal and revived to a viable state, wherein said microorganism is genetically different from modern day counterpart microorganisms as determined by FAME (fatty acid methyl ester) analysis.

44. The microorganism of claim 43, wherein it is over 25 million years old.

45. The microorganism of claim 43 wherein it is between 25 to 40 million years old.

46. The microorganism of claim 43 wherein it is from 250 years to 120 million years old.

47. The microorganism of claim 43 wherein the sequence homology of the ancient microorganism and its modern day counterpart is approximately 93–95% as determined by genetic analysis of portions of the 16S rDNA of both the ancient and modern day bacterial isolates.

48. The microorganism of claims 43,44,45,46 or 47, wherein the microorganism is a species selected from the group consisting of the genera of Actinomyces, Streptomyces, Penicillin, Bacillus, and Cladosporium.

* * * * *